US010620196B2

(12) United States Patent
Mehra et al.

(10) Patent No.: US 10,620,196 B2
(45) Date of Patent: Apr. 14, 2020

(54) ASSAYS FOR DETECTING ANALYTES IN SAMPLES AND KITS AND COMPOSITIONS RELATED THERETO

(71) Applicant: ABAXIS, INC., Union City, CA (US)

(72) Inventors: Rajesh K. Mehra, Union City, CA (US); Kenneth P. Aron, Union City, CA (US)

(73) Assignee: ABAXIS, INC., Union City, CA (US)

( * ) Notice: Subject to any disclaimer, the term of this patent is extended or adjusted under 35 U.S.C. 154(b) by 480 days.

(21) Appl. No.: 15/158,901

(22) Filed: May 19, 2016

(65) Prior Publication Data

US 2017/0108494 A1 Apr. 20, 2017

Related U.S. Application Data

(63) Continuation of application No. 12/971,968, filed on Dec. 17, 2010, now abandoned.

(60) Provisional application No. 61/287,637, filed on Dec. 17, 2009.

(51) Int. Cl.
| | |
|---|---|
| *G01N 33/543* | (2006.01) |
| *G01N 33/542* | (2006.01) |
| *G01N 33/569* | (2006.01) |

(52) U.S. Cl.
CPC ..... *G01N 33/54313* (2013.01); *G01N 33/542* (2013.01); *G01N 33/54346* (2013.01); *G01N 33/569* (2013.01); *G01N 2333/015* (2013.01); *G01N 2333/15* (2013.01); *G01N 2333/20* (2013.01); *G01N 2333/29* (2013.01); *G01N 2333/43526* (2013.01); *G01N 2333/44* (2013.01); *G01N 2333/4712* (2013.01); *G01N 2333/4737* (2013.01)

(58) Field of Classification Search
None
See application file for complete search history.

(56) References Cited

U.S. PATENT DOCUMENTS

| | | |
|---|---|---|
| 4,313,734 A | 2/1982 | Leuvering |
| 4,721,681 A | 1/1988 | Lentrichia et al. |
| 4,868,130 A | 9/1989 | Hargreaves |

(Continued)

FOREIGN PATENT DOCUMENTS

| | | |
|---|---|---|
| EP | 0194156 A1 | 9/1986 |
| EP | 0201755 A1 | 11/1986 |

(Continued)

OTHER PUBLICATIONS

Bui, et al., "Gold Nanoparticle Aggregation-Based Highly Sensitive DNA Detection Using Atomic Force Microscopy," Anal. Bioanal. Chem. (2007); vol. 388: 1185-1190.

(Continued)

*Primary Examiner* — Rebecca L Martinez
(74) *Attorney, Agent, or Firm* — Cooley, LLP

(57) ABSTRACT

The present invention provides methods of detecting analytes using particles having different physico-chemical properties, such as buoyancy, size, density, spectral characteristics, and/or binding properties, in solution-based sandwich assays and solution-based competition assays. The methods can be performed using rotors and bench-top centrifuges and provide for rapid, qualitative and quantitative detection of analytes. The present invention also provides kits that can be used to perform the methods, and mixtures containing particles suitable for the methods.

14 Claims, 9 Drawing Sheets

(56) References Cited

U.S. PATENT DOCUMENTS

| | | |
|---|---|---|
| 5,102,788 A | 4/1992 | Cole |
| 5,141,850 A | 8/1992 | Cole et al. |
| 5,160,701 A | 11/1992 | Brown et al. |
| 5,415,994 A | 5/1995 | Imrich et al. |
| 5,451,504 A | 9/1995 | Fitzpatrick et al. |
| 5,559,041 A | 9/1996 | Kang et al. |
| 5,646,001 A | 7/1997 | Terstappen et al. |
| 5,723,346 A | 3/1998 | Frengen |
| 6,146,836 A | 11/2000 | Barlow |
| 6,248,597 B1 | 6/2001 | Shinichi et al. |
| 7,344,893 B2 | 3/2008 | Kirkegaard et al. |
| 2004/0043507 A1 | 3/2004 | Song et al. |
| 2005/0221507 A1 | 10/2005 | Koo |
| 2010/0054981 A1 | 3/2010 | Liu |
| 2011/0151435 A1 | 6/2011 | Mehra et al. |

FOREIGN PATENT DOCUMENTS

| | | |
|---|---|---|
| EP | 0505636 A1 | 9/1992 |
| EP | 1420251 A1 | 5/2004 |
| WO | WO 1988/008534 A1 | 11/1988 |
| WO | WO 1989/011101 A1 | 11/1989 |
| WO | WO 1991/012336 A1 | 8/1991 |
| WO | WO 1994/015193 A1 | 7/1994 |
| WO | WO 2000/067027 A1 | 11/2000 |
| WO | WO 2003/046514 A2 | 6/2003 |
| WO | WO 2009/117510 A2 | 9/2009 |
| WO | WO 2011/084697 A2 | 7/2011 |

OTHER PUBLICATIONS

Chan, et al., "New Trends in Immunoassays," Adv Biochem Eng Biotechnol. (2008); vol. 109: 123-154.

Extended European Search Report in European Patent Application No. 10842653.7, dated Nov. 18, 2013, 9 pages.

Gupta, et al., "Characterization and Optimization of Gold Nanoparticle-Based Silver-Enhanced Immunoassays," Anal. Chem. (2007); vol. 79(10): 3810-3820.

Laderman, et al., "Rapid, Sensitive, and Specific Lateral-Flow Immunochromatographic Point-of-Care Device for Detection of Herpes Simplex Virus Type 2-Specific Immunoglobulin G Antibodies in Serum and Whole Blood," Clin. Vaccine Immunol. (2008); vol. 15(1): 159-163.

Lim, P.L., "One-Step 2-Minute Test to Detect Typhoid-Specific Antibodies Based on Particle Separation in Tubes." J Clin Microbiol. (Aug. 1998); 36(8): 2271-2278.

Nitin, et al., "Oligonucleotide-Coated Metallic Nanoparticles as a Flexible Platform for Molecular Imaging Agents," Bioconjug. Chem. (2007); vol. 18(6): 2090-2096.

PCT/US2010/061074, International Preliminary Report on Patentability, dated Jun. 19, 2012, 5 pages.

PCT/US2010/061074, International Search Report and Written Opinion, dated Sep. 29, 2011, 8 pages.

Sandwich Assay On Abaxis Rotor

Sandwich Assay On Abaxis Rotor

Sandwich Assay On Abaxis Rotor

Competitive Rotor Immunoassays

Latex Antibody - Bead B

Labeled Antigen-Bead A

ASSAYS FOR DETECTING ANALYTES IN SAMPLES AND KITS AND COMPOSITIONS RELATED THERETO

CROSS-REFERENCE TO RELATED APPLICATIONS

This application is a continuation of U.S. application Ser. No. 12/971,968, filed on Dec. 17, 2010, which claims the benefit of U.S. Provisional Application No. 61/287,637, filed Dec. 17, 2009, which is herein incorporated by reference in its entirety.

BACKGROUND OF THE INVENTION

In many fields of endeavor, and notably biomedical sciences, veterinary sciences, and environmental sciences, it is important to be able to detect molecules of interest (i.e., analytes) in samples that have been collected, for example, from test subjects (e.g., patients, laboratory and farm animals, pets, etc.) or the environment. To meet these needs, many different assays have been developed, ranging from lateral flow devices (e.g., home pregnancy tests), to immunoprecipitations and ELISAs, to mass spectrometry. These assays have proven very useful, but often suffer from a number of important drawbacks, such as being costly to implement, time consuming, technically complicated, hard to scale up for large sample sizes or large numbers of samples, etc.

There remains a need in the art for new assays for detecting analytes in samples.

SUMMARY OF THE INVENTION

The present invention is based, in part, on the discovery that particles having different physico-chemical properties, such as buoyancy, size, density, spectral characteristics, and/or binding properties, can be used in solution-based sandwich assays for rapid, qualitative and quantitative detection of analytes. The present invention is also based, in part, on the discovery that particles having different physico-chemical properties, such as buoyancy, size, density, spectral characteristics, and/or binding properties, can be used in solution-based competition assays for rapid, qualitative and quantitative detection of analytes. Accordingly, the present invention provides methods of detecting analytes, kits that can be used to perform such methods, and mixtures containing particles suitable for such methods.

In one aspect, the invention provides methods of detecting an analyte. In certain embodiments, the methods (e.g., solution-based sandwich assays) comprise:

mixing a sample with a population of first particles and a population of second particles to form a suspension, wherein the particles are capable of forming multi-particle complexes comprising a first particle, a second particle, and an analyte, removing multi-particle complexes formed upon said mixing from said suspension, and detecting the presence of first and/or second particles remaining in suspension, wherein a decrease in amount of first and/or second particles in suspension is indicative of the presence of the analyte in the sample.

In certain embodiments, the first and/or second particles are detectable in suspension. For example, in certain embodiments, the first and/or second particles scatter light or comprise a detectable color (e.g., visually or spectroscopically detectable color). In certain embodiments, the first and/or second particles comprise a label (e.g., fluorescent label). In certain embodiments, both the first and second particles comprise a label (e.g., different fluorescent labels or different chromophores). In certain embodiments, the first particles comprise a donor chromophore and the second particles comprise an acceptor chromophore, or vice versa, wherein the donor and acceptor chromophores are suitable for detecting interaction between the first and second particles by means of Förster Resonance Energy Transfer (FRET) analysis.

In certain embodiments, the first and/or second particles are colloidal particles (e.g., colloidal nanoparticles, nanotubes, core-shell structure particles, or hollow nanospheres). In certain embodiments, the first and/or second particles comprise gold, silver, platinum, copper, or mixed metal. In certain embodiments, the first and/or second particles comprise latex, polystyrene, polycarbonate, polyvinylidene fluoride, silica, a polymer having properties similar to any of the foregoing polymers, or a composite thereof. In certain embodiments, the first particles comprise gold, silver, platinum, copper, or mixed metal, and the second particles comprise latex, polystyrene, polycarbonate, polyvinylidene fluoride, silica, a polymer having properties similar to any of the foregoing polymers, or a composite thereof.

In certain embodiments, the first particles and the second particles have different physico-chemical properties. For example, in certain embodiments, the first particles have a greater buoyancy than the second particles, or vice versa. In certain embodiments, the first particles are smaller than the second particles, or vice versa. For example, in certain embodiments, the second particles have a diameter about 5 to about 50 times larger than the diameter of the first particles. Alternatively, in certain embodiments, the first particles have a diameter about 5 to about 50 times larger than the diameter of the second particles. In certain embodiments, the first particles have a greater density than the second particles, or vice versa. In certain embodiments, the first particles are smaller and more buoyant than the second particles. In certain embodiments, the first particles are smaller, more dense, and more buoyant than the second particles.

In certain embodiments, the first particles, second particles, or both first and second particles comprise an analyte-binding agent, such as an antibody, antigen, polypeptide, polynucleotide, nucleoprotein, aptamer, or ligand (e.g., a carbohydrate, lipid, steroid, vitamin, or other small molecule ligand). In certain embodiments, the first and second particles comprise different analyte-binding agents. In certain embodiments, the first and second particles comprise analyte-binding agents capable of binding to different parts of the same analyte (e.g., different domains, different epitopes, different subunits or molecules in a complex analyte, etc.). In certain embodiments, the first and second particles comprise analyte-binding agents capable of simultaneously binding to the same analyte. In certain embodiments, the first particles comprise a first antibody capable of recognizing a first epitope on an analyte, the second particles comprise a second antibody capable of recognizing a second epitope on the same analyte, and the first and second epitopes are different (e.g., non-overlapping). For example, the first and second epitopes can be on different surfaces of a simple analyte or different subunits or molecules in a complex analyte. In other embodiments, the first particles comprise an antigen capable of being recognized by an analyte (e.g., an antibody analyte, such as a disease-specific antibody or an auto-antibody) and the second particles comprise a protein or antibody capable of recognizing the analyte. For example, the second particle can comprise a protein that is an antibody-binding protein, such as Protein A, Protein G, or Protein L, or an antibody that binds to an antibody constant region (e.g., an anti-IgG or anti-IgM antibody).

In certain embodiments, removing said multi-particle complexes comprises allowing gravity to pellet said complexes. In other embodiments, removing said multi-particle complexes comprises applying a force. For example, in certain embodiments, removing said multi-particle complexes comprises applying centrifugal force to said suspension (e.g., by spinning the suspension in a rotor). In certain embodiments, the gravity or force applied pellets said multi-particle complexes but does not pellet first particles and second particles that are not present in one of said multi-particle complexes. In certain embodiments, the gravity or force applied pellets said multi-particle complexes and either said first particles (e.g., free first particles and first particles present in a multi-particle complex) or said second particles (e.g., free second particles and second particles present in a multi-particle complex), but not both said first particles and said second particles.

In certain embodiments, the analyte is present in a biological sample (e.g., blood, serum, urine, etc.) or an environmental sample (e.g., a sample of ground water, river, lake, waste water, etc.). In certain embodiments, the analyte is a marker (e.g., an antigen marker or antibody marker) for a disease. For example, in certain embodiments, the analyte is a cancer-related antigen, a viral antigen, a bacterial antigen, a fungal antigen, an autoimmune-associated antigen, a cardiovascular disease-associated antigen, or an antibody to any of the foregoing antigens.

In certain embodiments, the invention provides methods (e.g., solution-based sandwich assays) for detecting an analyte, the methods comprising:

mixing a sample with a population of first particles and a population of second particles to form a suspension, wherein the particles are capable of forming multi-particle complexes comprising a first particle, a second particle, and an analyte, removing said second particles from said suspension, and detecting the presence of first particles remaining in suspension, wherein a decrease in amount of first particles in suspension is indicative of the presence of the analyte in the sample.

In certain embodiments, the first particles are detectable in suspension. For example, in certain embodiments, the first particles scatter light or comprise a detectable color (e.g., visually or spectroscopically detectable color). In certain embodiments, the first particles comprise a label (e.g., a fluorescent label). In certain embodiments, both the first and second particles comprise a label (e.g., different fluorescent labels or different chromophores). In certain embodiments, the first particles comprise a donor chromophore and the second particles comprise an acceptor chromophore, or vice versa, wherein the donor and acceptor chromophores are suitable for detecting interaction between the first and second particles by means of FRET analysis.

In certain embodiments, the first particles are colloidal particles (e.g., colloidal nanoparticles, nanotubes, core-shell structure particles, or hollow nanospheres). In certain embodiments, the first and second particles are colloidal particles (e.g., colloidal nanoparticles, nanotubes, core-shell structure particles, or hollow nanospheres). In certain embodiments, the first particles comprise gold, silver, platinum, copper, or mixed metal. In certain embodiments, the first particles comprise latex, polystyrene, polycarbonate, polyvinylidene fluoride, silica, a polymer having properties similar to any of the foregoing polymers, or a composite thereof. In certain embodiments, the first and second particles comprise latex, polystyrene, polycarbonate, polyvinylidene fluoride, silica, a polymer having properties similar to any of the foregoing polymers, or a composite thereof. In certain embodiments, the first particles comprise gold, silver, platinum, copper, or mixed metal, and the second particles comprise latex, polystyrene, polycarbonate, polyvinylidene fluoride, silica, a polymer having properties similar to any of the foregoing polymers, or a composite thereof.

In certain embodiments, the first particles and second particles have different physico-chemical properties. For example, in certain embodiments, the first particles have a greater buoyancy than the second particles. In certain embodiments, the first particles are smaller than the second particles. For example, in certain embodiments, the second particles have a diameter about 5 to about 50 times larger than the diameter of the first particles. In certain embodiments, the first particles have a greater density than the second particles. In other embodiments, the second particles have a greater density than the first particles. In certain embodiments, the first particles are smaller and more buoyant than the second particles. In certain embodiments, the first particles are smaller, more dense, and more buoyant than the second particles.

In certain embodiments, the first particles, second particles, or both the first and second particles comprise an analyte-binding agent, such as an antibody, antigen, polypeptide, polynucleotide, nucleoprotein, aptamer, or ligand (e.g., a carbohydrate, lipid, steroid, vitamin, or other small molecule ligand). In certain embodiments, the first and second particles comprise different analyte-binding agents. In certain embodiments, the first and second particles comprise analyte-binding agents capable of binding to different parts of the same analyte (e.g., different domains, different epitopes, different subunits or molecules in a complex analyte, etc.). In certain embodiments, the first and second particles comprise analyte-binding agents capable of simultaneously binding to the same analyte. In certain embodiments, the first particles comprise a first antibody capable of recognizing a first epitope on an analyte, the second particles comprise a second antibody capable of recognizing a second epitope on the same analyte, and the first and second epitopes are different (e.g., non-overlapping). For example, the first and second epitopes can be on different surfaces of a simple analyte or different subunits or molecules in a complex analyte. In other embodiments, the first particles comprise an antigen capable of being recognized by an analyte (e.g., an antibody analyte, such as a disease-specific antibody or an auto-antibody) and the second particles comprise a protein or antibody capable of recognizing the analyte. For example, the second particle can comprise a protein that is an antibody-binding protein, such as Protein A, Protein G, or Protein L, or an antibody that binds to an antibody constant region (e.g., an anti-IgG or anti-IgM antibody).

In certain embodiments, removing said second particles comprises removing said multi-particle complexes. In certain embodiments, removing said second particles comprises allowing gravity to pellet said second particles (and said multi-particle complexes). In other embodiments, removing said second particles comprises applying a force. For example, in certain embodiments, removing said second particles comprises applying centrifugal force to said suspension (e.g., by spinning the suspension in a rotor). In certain embodiments, the gravity or force applied pellets said second particles but does not pellet first particles that are not complexed to one of the second particles.

In certain embodiments, the analyte is present in a biological sample (e.g., blood, serum, urine, etc.) or an environmental sample (e.g., a sample of ground water, river, lake, waste water, etc.). In certain embodiments, the analyte is a marker (e.g., an antigen marker or antibody marker) for a disease. For example, in certain embodiments, the analyte is a cancer-related antigen, a viral antigen, a bacterial antigen, a fungal antigen, an autoimmune-associated antigen, a cardiovascular disease-associated antigen, or an antibody to any of the foregoing antigens.

In other embodiments, the invention provides methods (e.g., solution-based competition assays) for detecting an analyte, the methods comprising:

mixing a sample with a population of first particles and a population of second particles to form a suspension, wherein the first particles comprise an analyte, and wherein the particles are capable of forming multi-particle complexes comprising a first particle and a second particle, removing multi-particle complexes formed upon said mixing from said suspension, and detecting the presence of first and/or second particles remaining in suspension, wherein an increase in amount of first and/or second particles in suspension is indicative of the presence of the analyte in the sample.

In certain embodiments, the first and/or second particles are detectable in suspension. For example, in certain embodiments, the first and/or second particles scatter light or comprise a detectable color (e.g., visually or spectroscopically detectable color). In certain embodiments, the first and/or second particles comprise a label (e.g., fluorescent label). In certain embodiments, both the first and second particles comprise a label (e.g., different fluorescent labels or different chromophores). In certain embodiments, the first particles comprise a donor chromophore and the second particles comprise an acceptor chromophore, or vice verse, wherein the donor and acceptor chromophores are suitable for detecting interaction between the first and second particles by means of FRET analysis.

In certain embodiments, the first and/or second particles are colloidal particles (e.g., colloidal nanoparticles, nanotubes, core-shell structure particles, or hollow nanospheres). In certain embodiments, the first and/or second particles comprise gold, silver, platinum, copper, or mixed metal. In certain embodiments, the first and/or second particles comprise latex, polystyrene, polycarbonate, polyvinylidene fluoride, silica, a polymer having properties similar to any of the foregoing polymers, or a composite thereof. In certain embodiments, the first particles comprise gold, silver, platinum, copper, or mixed metal, and the second particles comprise latex, polystyrene, polycarbonate, polyvinylidene fluoride, silica, a polymer having properties similar to any of the foregoing polymers, or a composite thereof.

In certain embodiments, the first particles and the second particles have different physico-chemical properties. For example, in certain embodiments, the first particles have a greater buoyancy than the second particles, or vice versa. In certain embodiments, the first particles are smaller than the second particles, or vice versa. For example, in certain embodiments, the second particles have a diameter about 5 to about 50 times larger than the diameter of the first particles. Alternatively, in certain embodiments, the first particles have a diameter about 5 to about 50 times larger than the diameter of the second particles. In certain embodiments, the first particles have a greater density than the second particles, or vice versa. In certain embodiments, the first particles are smaller and more buoyant than the second particles. In certain embodiments, the first particles are smaller, more dense, and more buoyant than the second particles.

In certain embodiments, the second particles comprise an analyte-binding agent, such as an antibody, antigen, polypeptide, polynucleotide, nucleoprotein, aptamer, or ligand (e.g., a carbohydrate, lipid, steroid, vitamin, or other small molecule ligand). In certain embodiments, the analyte-binding agent is capable of binding to analyte present on said first particles.

In certain embodiments, removing said multi-particle complexes comprises allowing gravity to pellet said multi-particle complexes. In other embodiments, removing said multi-particle complexes comprises applying a force. For example, in certain embodiments, removing said multi-particle complexes comprises applying centrifugal force to said suspension (e.g., by spinning the suspension in a rotor). In certain embodiments, the gravity or force applied pellets said multi-particle complexes but does not pellet first particles and second particles that are not present in one of said multi-particle complexes. In certain embodiments, the gravity or force applied pellets said multi-particle complexes and either said first particles (e.g., free first particles and first particles present in a multi-particle complex) or said second particles (e.g., free second particles and second particles present in a multi-particle complex), but not both of said first particles and said second particles.

In certain embodiments, the analyte is present in a biological sample (e.g., blood, serum, urine, etc.) or an environmental sample (e.g., a sample of ground water, river, lake, waste water, etc.). In certain embodiments, the analyte is a marker (e.g., an antigen marker or an antibody marker) for a disease. For example, in certain embodiments, the analyte is a cancer-related antigen, a viral antigen, a bacterial antigen, a fungal antigen, an autoimmune-associated antigen, a cardiovascular disease-associated antigen, or an antibody to any of the foregoing antigens.

In still other embodiments, the invention provides methods (e.g., solution-based competition assays) for detecting an analyte, the methods comprising:

mixing a sample with a population of first particles and a population of second particles to form a suspension, wherein the first particles comprise an analyte, and wherein the particles are capable of forming multi-particle complexes comprising a first particle and a second particle, removing said second particles from said suspension, and detecting the presence of first particles remaining in suspension, wherein an increase in amount of first particles in suspension is indicative of the presence of the analyte in the sample.

In certain embodiments, the first particles are detectable in suspension. For example, in certain embodiments, the first particles scatter light or comprise a detectable color (e.g., visually or spectroscopically detectable color). In certain embodiments, the first particles comprise a label (e.g., a fluorescent label). In certain embodiments, both the first and second particles comprise a label (e.g., different fluorescent labels or different chromophores). In certain embodiments, the first particles comprise a donor chromophore and the second particles comprise an acceptor chromophore, or vice verse, wherein the donor and acceptor chromophores are suitable for detecting interaction between the first and second particles by means of FRET analysis.

In certain embodiments, the first and/or second particles are colloidal particles (e.g., colloidal nanoparticles, nanotubes, core-shell structure particles, or hollow nanospheres). In certain embodiments, the first and/or second particles comprise gold, silver, platinum, copper, or mixed metal. In certain embodiments, the first and/or second particles comprise latex, polystyrene, polycarbonate, polyvinylidene fluoride, silica, a polymer having properties similar to any of the foregoing polymers, or a composite thereof. In certain embodiments, the first particles comprise gold, silver, platinum, copper, or mixed metal, and the second particles comprise latex, polystyrene, polycarbonate, polyvinylidene fluoride, silica, a polymer having properties similar to any of the foregoing polymers, or a composite thereof.

In certain embodiments, the first particles and the second particles have different physico-chemical properties. For example, in certain embodiments, the first particles have a greater buoyancy than the second particles. In certain embodiments, the first particles are smaller than the second particles. For example, in certain embodiments, the second particles have a diameter about 5 to about 50 times larger than the diameter of the first particles. In certain embodiments, the first particles have a greater density than the second particles. In other embodiments, the second particles have a greater density than the first particles. In certain embodiments, the first particles are smaller and more buoyant than the second particles. In certain embodiments, the first particles are smaller, more dense, and more buoyant than the second particles.

In certain embodiments, the second particles comprise an analyte-binding agent, such as an antibody, antigen, polypeptide, polynucleotide, nucleoprotein, aptamer, or ligand (e.g., a carbohydrate, lipid, steroid, vitamin, or other small molecule ligand). In certain embodiments, the analyte-binding agent is capable of binding to analyte present on said first particles.

In certain embodiments, removing said second particles comprises removing said multi-particle complexes. In certain embodiments, removing said second particles comprises allowing gravity to pellet said second particles (and said multi-particle complexes). In other embodiments, removing said second particles comprises applying a force. For example, in certain embodiments, removing said second particles comprises applying centrifugal force to said suspension (e.g., by spinning the suspension in a rotor). In certain embodiments, the gravity or force applied pellets said second particles but does not pellet first particles that are not complexed to one of the second particles.

In certain embodiments, the analyte is present in a biological sample (e.g., blood, serum, urine, etc.) or an environmental sample (e.g., a sample of ground water, river, lake, waste water, etc.). In certain embodiments, the analyte is a marker (e.g., an antigen marker or an antibody marker) for a disease. For example, in certain embodiments, the analyte is a cancer-related antigen, a viral antigen, a bacterial antigen, a fungal antigen, an autoimmune-associated antigen, a cardiovascular disease-associated antigen, or an antibody to any of the foregoing antigens.

In another aspect, the invention provides kits comprising a population of first particles and a population of second particles suitable for use in methods of the invention. In certain embodiments, the first and second particles are capable of forming multi-particle complexes. In certain embodiments, the first and second particles are suitable for use in solution-based competition assays. For example, in certain embodiments, the first and second particles are capable of forming multi-particle complexes wherein free analyte disrupts (e.g., competitively inhibits) formation of said multi-particle complexes. In other embodiments, the first and second particles are suitable for use in solution-based sandwich assays (e.g., direct or indirect sandwich assays). For example, in certain embodiments, the first and second particles are capable of forming multi-particle complexes comprising a first particle, a second particle, and an analyte. In certain related embodiments, the first and second particles are capable of forming multi-particle complexes, wherein said first particle and said second particle each bind to the same analyte, and wherein said analyte links said first particle to said second particle.

In certain embodiments, said first and/or second particles are detectable in suspension. For example, in certain embodiments, the first and/or second particles scatter light or comprise a detectable color (e.g., visually or spectroscopically detectable color). In certain embodiments, the first and/or second particles comprise a label (e.g., a fluorescent label). In certain embodiments, both the first and second particles comprise a label (e.g., different fluorescent labels or different chromophores). In certain embodiments, the first particles comprise a donor chromophore and the second particles comprise an acceptor chromophore, or vice verse, wherein the donor and acceptor chromophores are suitable for detecting interaction between the first and second particles by means of Förster Resonance Energy Transfer (FRET) analysis.

In certain embodiments, the first and/or second particles are colloidal particles (e.g., colloidal nanoparticles, nanotubes, core-shell structure particles, or hollow nanospheres). In certain embodiments, the first and/or second particles comprise gold, silver, platinum, copper, or mixed metal. In certain embodiments, the first and/or second particles comprise latex, polystyrene, polycarbonate, polyvinylidene fluoride, silica, a polymer having properties similar to any of the foregoing polymers, or a composite thereof. In certain embodiments, the first particles comprise gold, silver, platinum, copper, or mixed metal, and the second particles comprise latex, polystyrene, polycarbonate, polyvinylidene fluoride, silica, a polymer having properties similar to any of the foregoing polymers, or a composite thereof.

In certain embodiments, the first particles and the second particles have different physico-chemical properties. For example, in certain embodiments, the first particles have a greater buoyancy than the second particles. In certain embodiments, the first particles are smaller than the second particles. For example, in certain embodiments, the second particles have a diameter about 5 to about 50 times larger than the diameter of the first particles. In other embodiments, the first particles have a diameter about 5 to about 50 times larger than the diameter of the second particles. In certain embodiments, the first particles have a greater density than the second particles, or vice versa. In certain embodiments, the first particles are smaller and more buoyant than the second particles. In certain embodiments, the first particles are smaller, more dense, and more buoyant than the second particles.

In certain embodiments, the first particles comprise an analyte and the second particles comprise a corresponding analyte-binding agent, such as an antibody, antigen, polypeptide, polynucleotide, nucleoprotein, aptamer, or ligand (e.g., a carbohydrate, lipid, steroid, vitamin, or other small molecule ligand). In certain embodiments, both the first and second particles comprise an analyte-binding agent, such as an antibody, antigen, polypeptide, polynucleotide, nucleoprotein, aptamer, or ligand (e.g., a carbohydrate, lipid, steroid, vitamin, or other small molecule ligand), wherein the analyte-binding agents bind to the same analyte.

In certain embodiments, the first and second particles comprise different analyte-binding agents. In certain embodiments, the first and second particles comprise analyte-binding agents capable of binding to different parts of the same analyte (e.g., different domains, different epitopes, different subunits or molecules in a complex analyte, etc.). In certain embodiments, the first and second particles comprise analyte-binding agents capable of simultaneously binding to the same analyte. In certain embodiments, the first particles comprise a first antibody capable of recognizing a first epitope on an analyte, the second particles comprise a second antibody capable of recognizing a second epitope on the same analyte, and the first and second epitopes are different (e.g., non-overlapping). For example, the first and second epitopes can be on different surfaces of a simple analyte or different subunits or molecules in a complex analyte. In other embodiments, the first particles comprise an antigen capable of being recognized by an analyte (e.g., an antibody analyte, such as a disease-specific antibody or an auto-antibody) and the second particles comprise a protein or antibody capable of recognizing the analyte. For example, the second particle can comprise a protein that is an antibody-binding protein, such as Protein A, Protein G, or Protein L, or an antibody that binds to an antibody constant region (e.g., an anti-IgG or anti-IgM antibody).

In certain embodiments, the population of first particles is in solid (e.g., lyophilized) form. In certain embodiments, the population of second particles is in solid (e.g., lyophilized) form. In certain embodiments, the population of first particles and the population of second particles are in solid (e.g., lyophilized) form.

In certain embodiments, the kit further comprises a container (e.g., a test tube, bottle, or cuvette) that comprises said population of first particles, said population of second particles, or both populations of said first and said second particles. In certain embodiments, the kit further comprises a rotor, wherein said rotor comprises or is capable of holding a container (e.g., a cuvette) that comprises said population of first particles, said population of second particles, or both populations of said first and said second particles.

In certain embodiments, the kit further comprises instructions (e.g., instructions for using the contents of the kit to carry out a method of the invention).

In yet another aspect, the invention provides mixtures comprising a population of first particles, a population of second particles, and, optionally, an analyte. In certain embodiments, the mixture is part of a solution-based competition assay. For example, in certain embodiments, the first and second particles are capable of forming multi-particle complexes wherein free analyte disrupts (e.g., competitively inhibits) formation of said multi-particle complexes. In other embodiments, the mixture is part of a solution-based sandwich assay (e.g., a direct or indirect sandwich assay). For example, in certain embodiments, the first and second particles are capable of forming multi-particle complexes comprising a first particle, a second particle, and an analyte. In certain related embodiments, the first and second particles are capable of forming multi-particle complexes, wherein said first particle and said second particle each bind to the same analyte, and wherein said analyte links said first particle to said second particle.

In certain embodiments, said first and/or second particles are detectable in suspension. For example, in certain embodiments, the first and/or second particles scatter light or comprise a detectable color (e.g., visually or spectroscopically detectable color). In certain embodiments, the first and/or second particles comprise a label (e.g., a fluorescent label). In certain embodiments, both the first and second particles comprise a label (e.g., different fluorescent labels or different chromophores). In certain embodiments, the first particles comprise a donor chromophore and the second particles comprise an acceptor chromophore, or vice versa, wherein the donor and acceptor chromophores are suitable for detecting interaction between the first and second particles by means of Förster Resonance Energy Transfer (FRET) analysis.

In certain embodiments, the first and/or second particles are colloidal particles (e.g., colloidal nanoparticles, nanotubes, core-shell structure particles, or hollow nanospheres). In certain embodiments, the first and/or second particles comprise gold, silver, platinum, copper, or mixed metal. In certain embodiments, the first and/or second particles comprise latex, polystyrene, polycarbonate, polyvinylidene fluoride, silica, a polymer having properties similar to any of the foregoing polymers, or a composite thereof. In certain embodiments, the first particles comprise gold, silver, platinum, copper, or mixed metal, and the second particles comprise latex, polystyrene, polycarbonate, polyvinylidene fluoride, silica, a polymer having properties similar to any of the foregoing polymers, or a composite thereof.

In certain embodiments, the first particles and the second particles have different physico-chemical properties. For example, in certain embodiments, the first particles have a greater buoyancy than the second particles, or vice versa. In certain embodiments, the first particles are smaller than the second particles, or vice versa. For example, in certain embodiments, the second particles have a diameter about 5 to about 50 times larger than the diameter of the first particles. Alternatively, in certain embodiments, the first particles have a diameter about 5 to about 50 times larger than the diameter of the second particles. In certain embodiments, the first particles have a greater density than the second particles, or vice versa. In certain embodiments, the first particles are smaller and more buoyant than the second particles. In certain embodiments, the first particles are smaller, more dense, and more buoyant than the second particles.

In certain embodiments, the first particles comprise an analyte and the second particles comprise a corresponding analyte-binding agent, such as an antibody, antigen, polypeptide, polynucleotide, nucleoprotein, aptamer, or ligand (e.g., a carbohydrate, lipid, steroid, vitamin, or other small molecule ligand). In other embodiments, both the first and second particles comprise an analyte-binding agent, such as an antibody, antigen, polypeptide, polynucleotide, nucleoprotein, aptamer, or ligand (e.g., a carbohydrate, lipid, steroid, vitamin, or other small molecule ligand), wherein the analyte-binding agents bind to the same analyte.

In certain embodiments, the first and second particles comprise different analyte-binding agents. In certain embodiments, the first and second particles comprise analyte-binding agents capable of binding to different parts of the same analyte (e.g., different domains, different epitopes, different subunits or molecules in a complex analyte, etc.). In certain embodiments, the first and second particles comprise analyte-binding agents capable of simultaneously binding to the same analyte. In certain embodiments, the first particles comprise a first antibody capable of recognizing a first epitope on the analyte, the second particles comprise a second antibody capable of recognizing a second epitope on the analyte, and the first and second epitopes are different (e.g., non-overlapping). For example, the first and second epitopes can be on different surfaces of a simple analyte or different subunits or molecules in a complex analyte. In other embodiments, the first particles comprise an antigen capable of being recognized by an analyte (e.g., an antibody analyte, such as a disease-specific antibody or an auto-antibody) and the second particles comprise a protein or antibody capable of recognizing the analyte. For example, the second particle can comprise a protein that is an antibody-binding protein, such as Protein A, Protein G, or Protein L, or an antibody that binds to an antibody constant region (e.g., an anti-IgG or anti-IgM antibody).

The invention and additional embodiments thereof will be set forth in greater detail in the detailed description that follows.

BRIEF DESCRIPTION OF THE DRAWINGS

FIG. 1 depicts a sandwich assay of the invention.

FIG. 2 depicts a competition assay of the invention.

DETAILED DESCRIPTION OF THE INVENTION

Figure 1A:
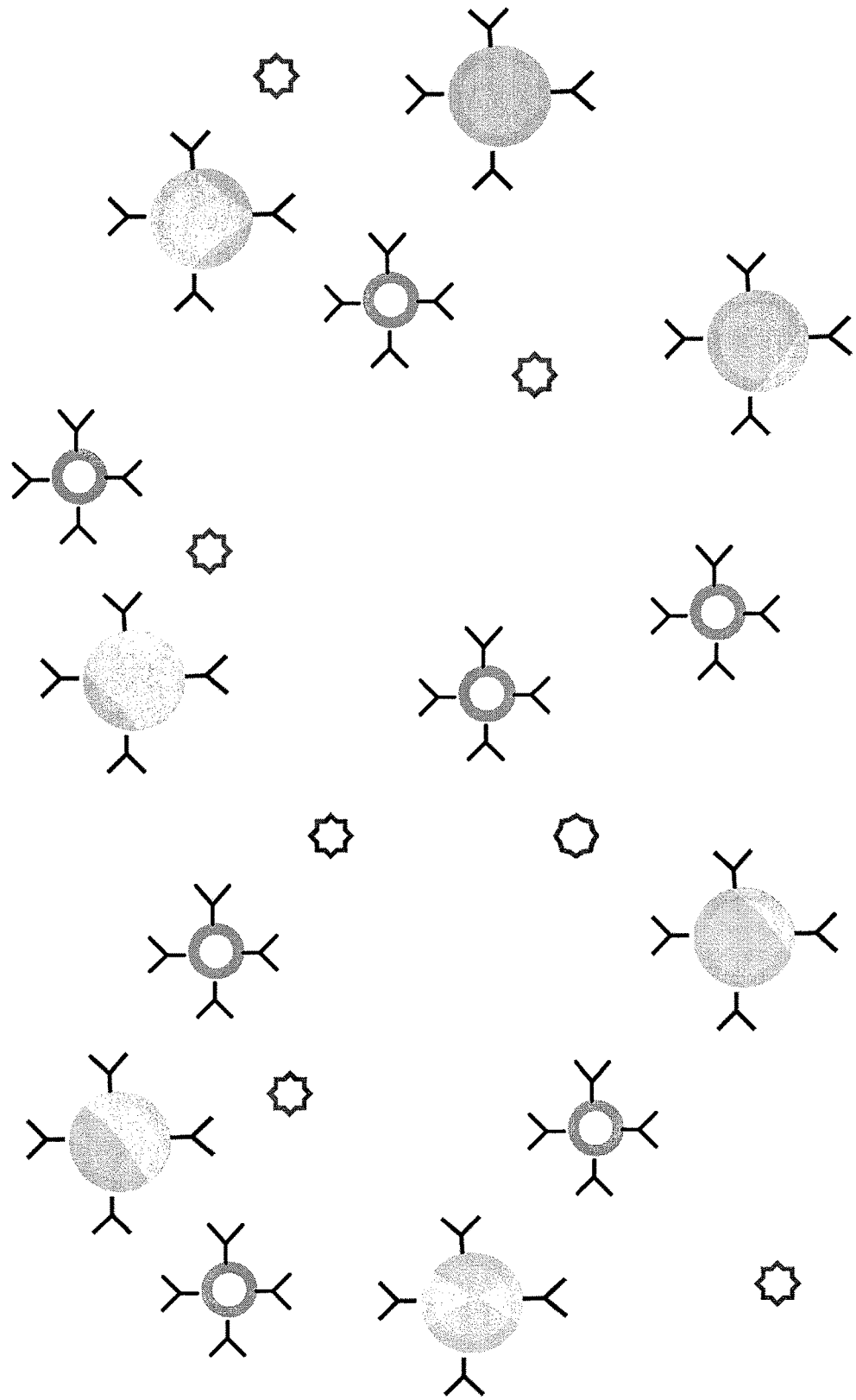
FIG. 1a shows a population of first particles and a population of second particles mixed with an analyte. The first and second particles differ from one another on the basis of buoyancy, size, and density. The branched structures projecting from the first and second particles are analyte-binding agents.
Figure 1B:
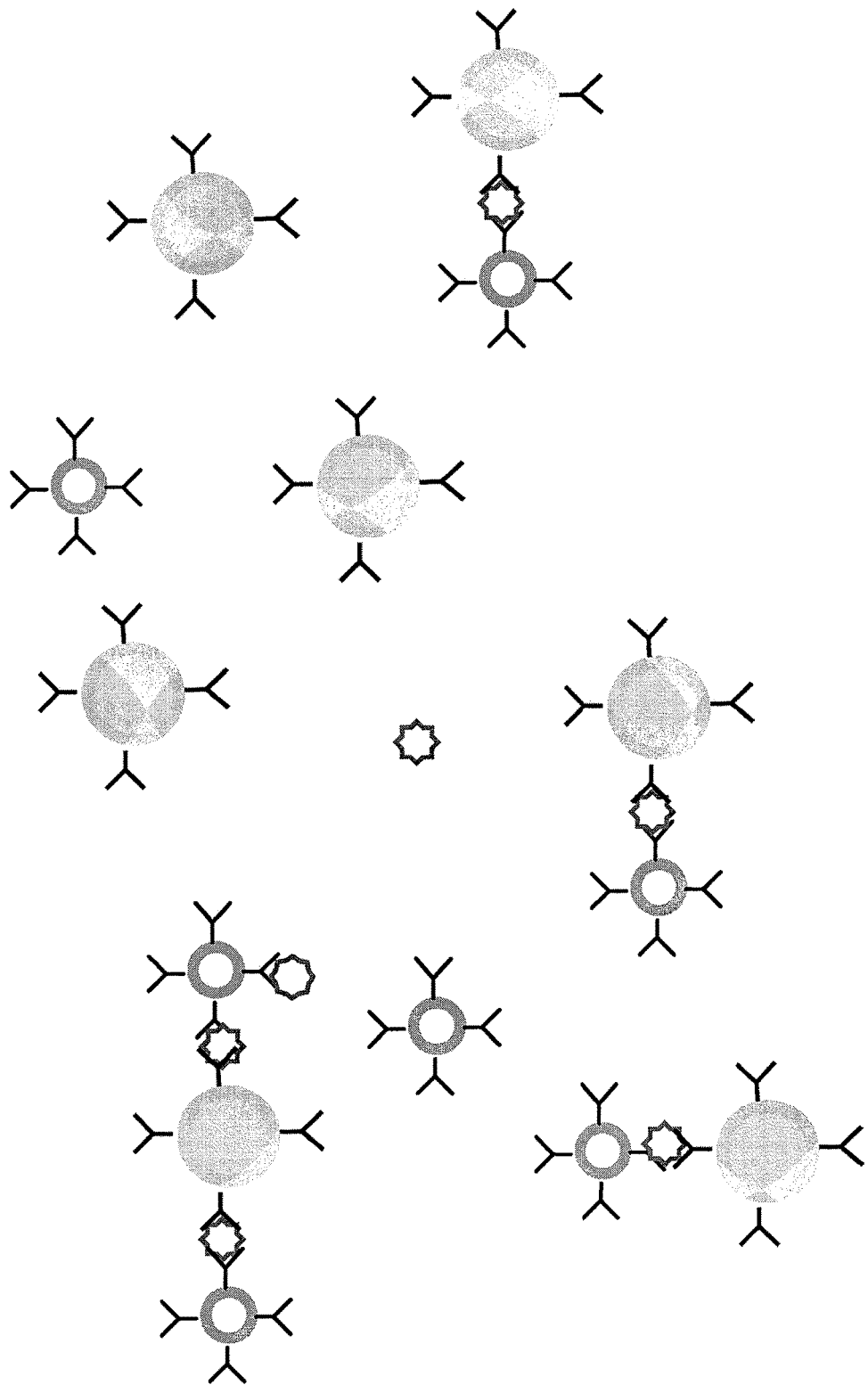
FIG. 1b shows the formation of complexes between first particles and second particles, wherein free analyte molecules bind to both first and second particles and thereby facilitate complex formation.
Figure 1C:
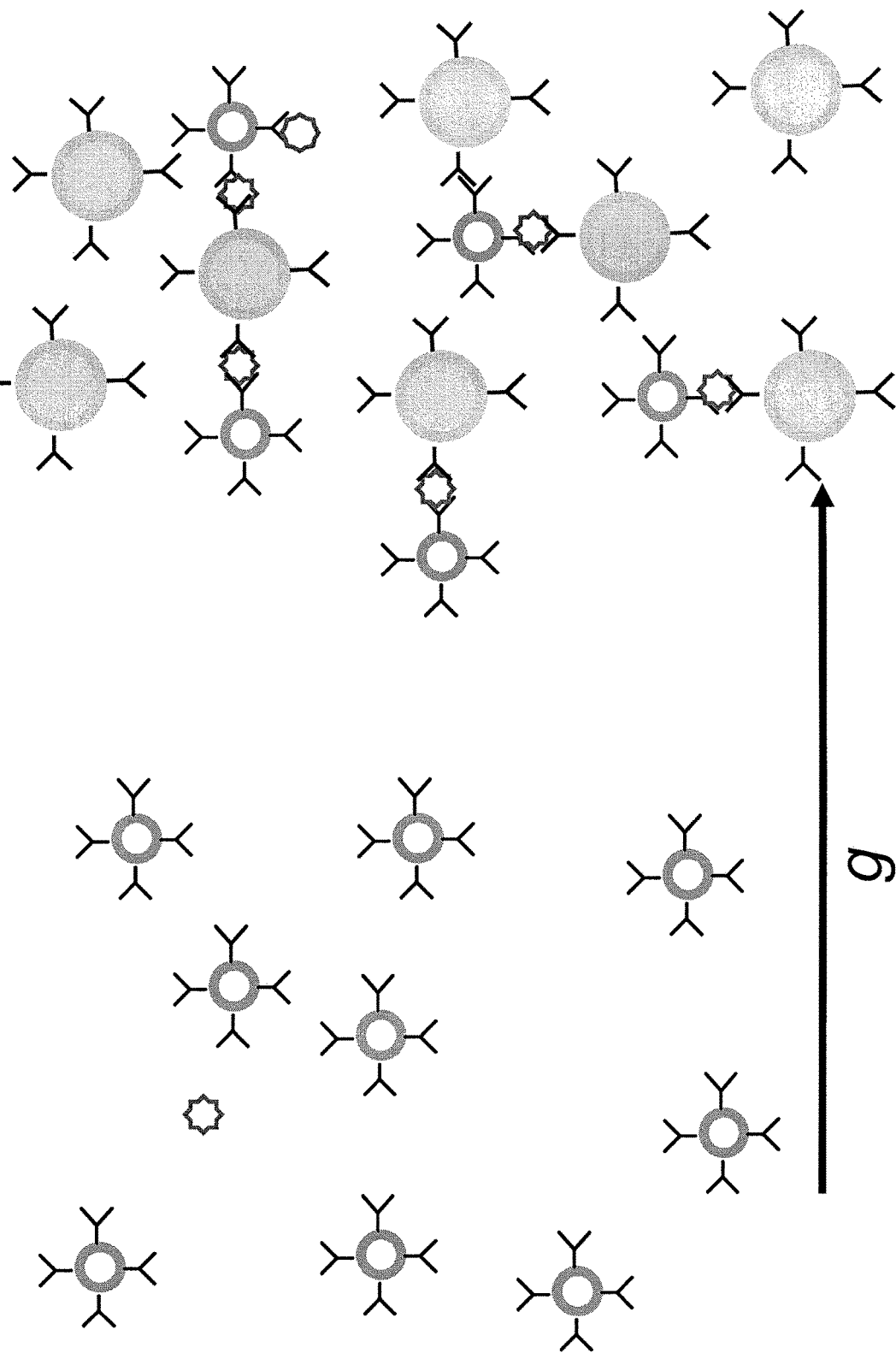
FIG. 1c shows how the application of force, such as gravity or centrifugal force, can lead to separation of first particles from second particles, with the larger particles leaving solution to form a pellet along with any complexes that include the larger particles.
Figure 1D:
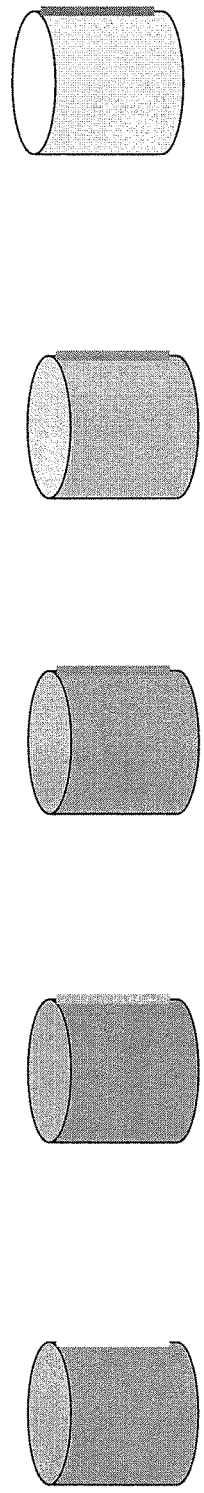
FIG. 1d shows one relationship between (1) the absorbance of the mixture of first and second particles and analyte, and (2) the concentration of analyte in the mixture, following the application of an appropriate force. Initially, the absorbance of the mixture goes down as the analyte concentration goes up, reflecting the fact that increased analyte concentration leads to increased complex formation, with the complexes being pelletted upon application of force.
Figure 1D:
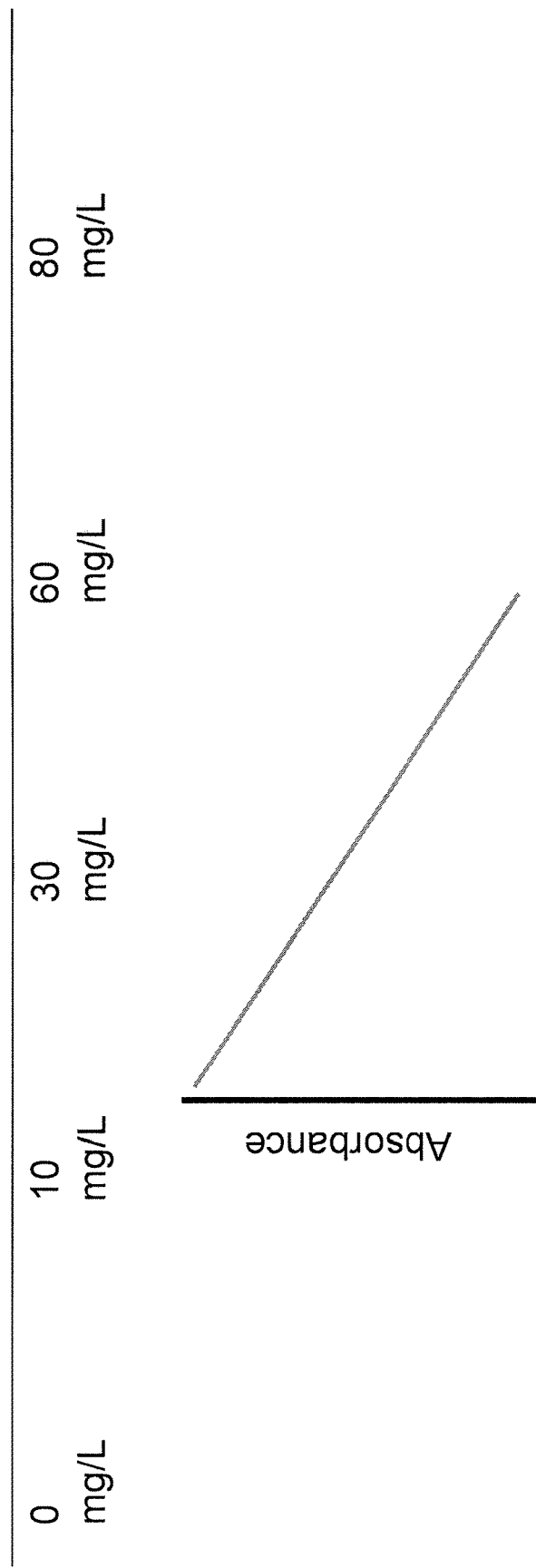
Figure 2A:
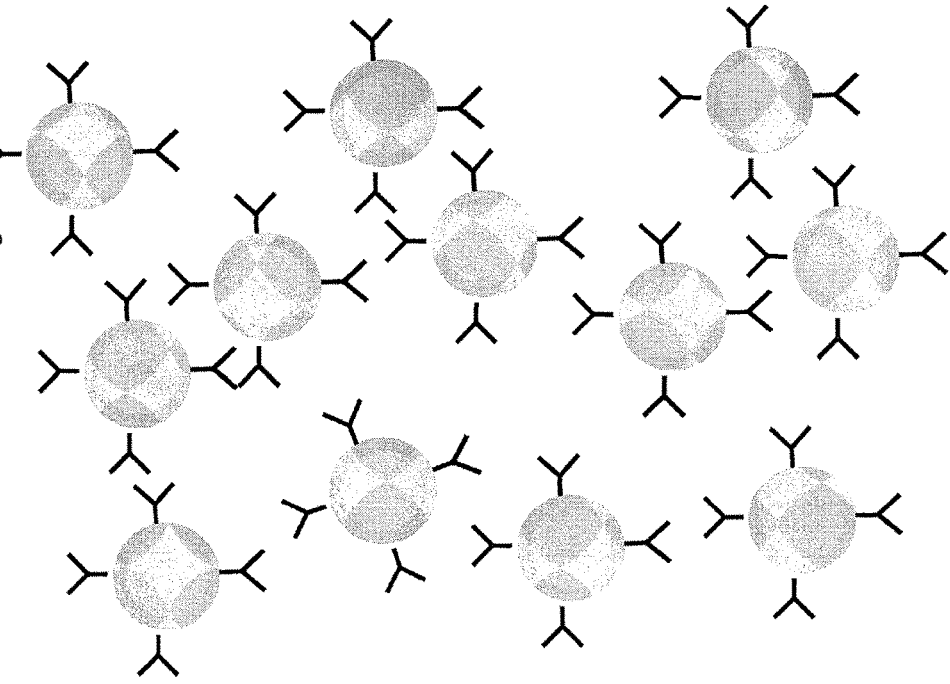
FIG. 2a shows a population of first particles and a population of second particles, wherein particles of the first population are coated with analyte and particles of the second population are coated with corresponding analyte-binding molecules. The particles of the two populations further differ from one another on the basis of buoyancy, size, and density.
Figure 2A:
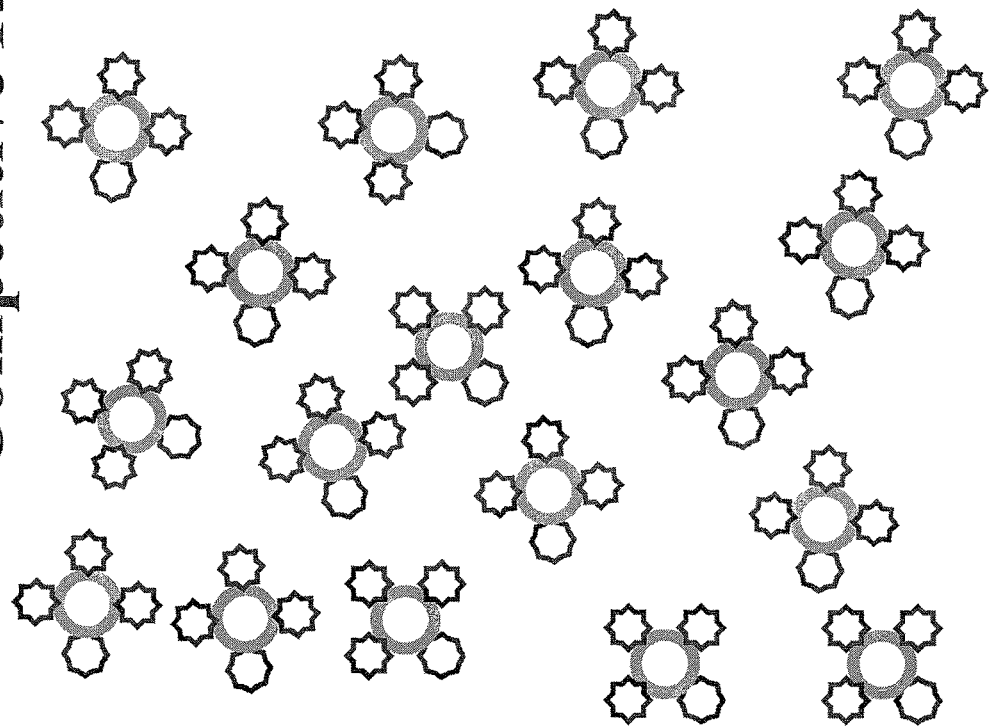
Figure 2B:
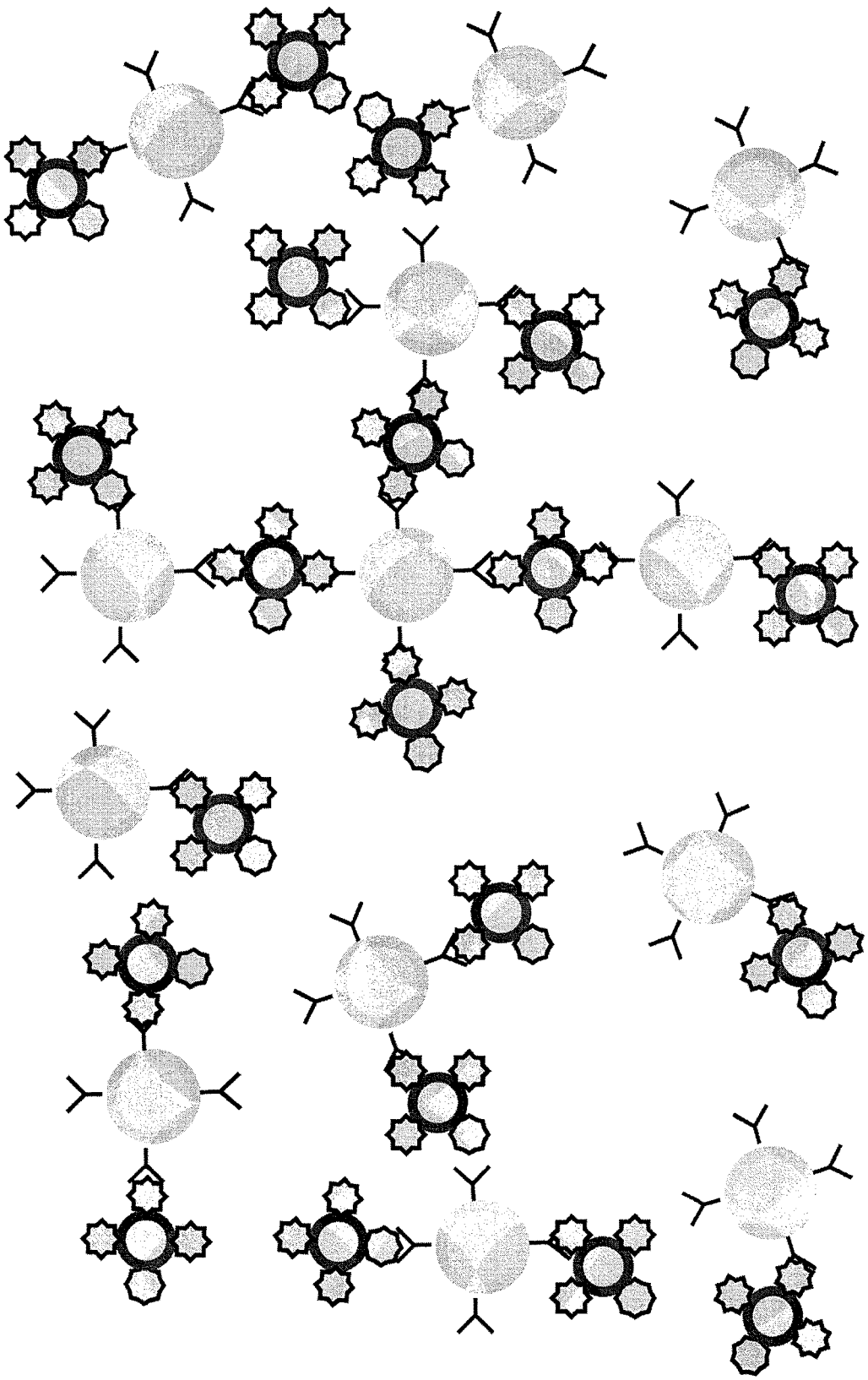
FIG. 2b shows the formation of complexes between particles of the first and second populations upon mixing.
Figure 2C:
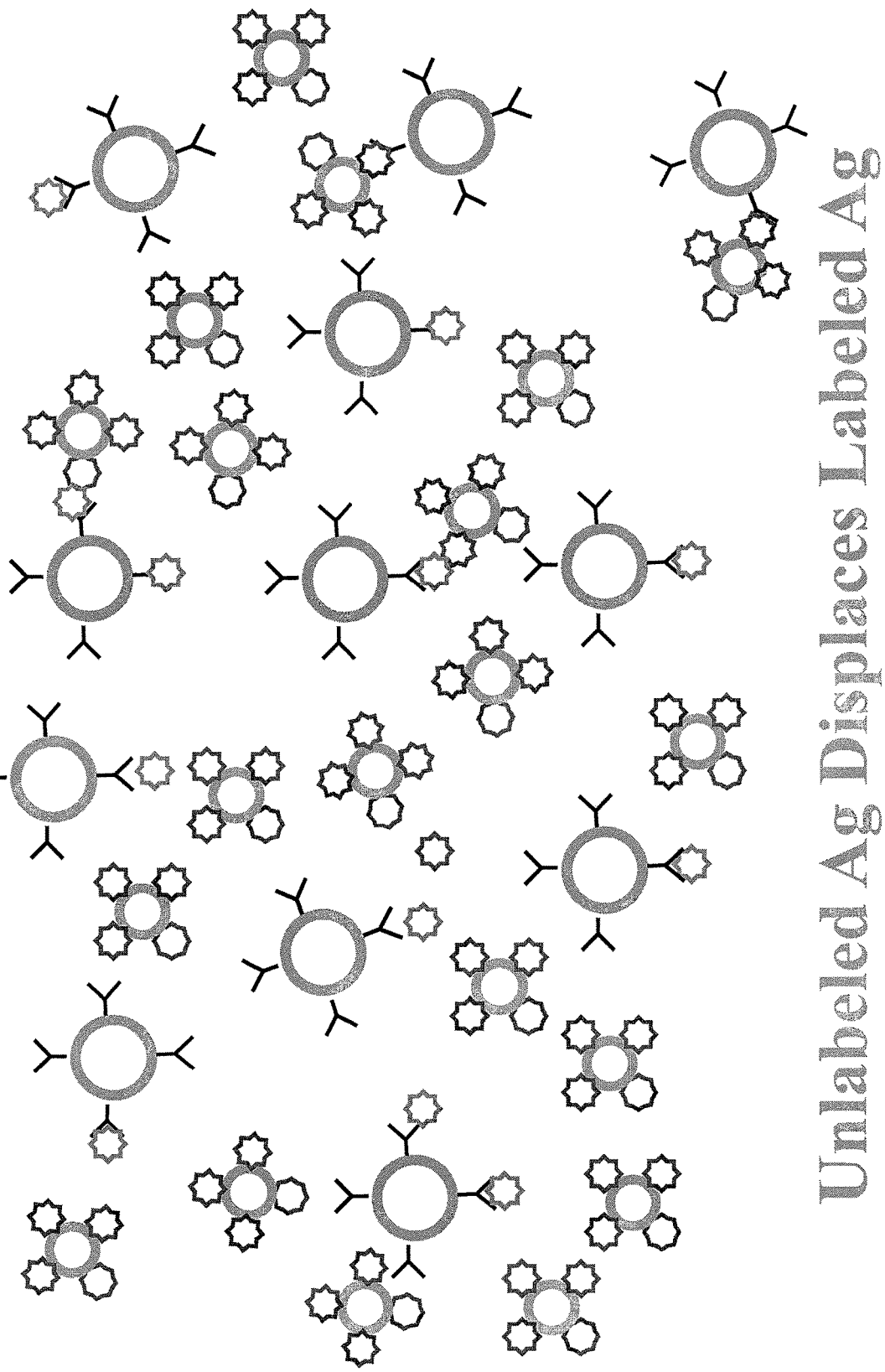
FIG. 2c shows free analyte molecules competing with particles of the first population for binding to the analyte-binding molecules present on particles of the second population, and thereby preventing complex formation and/or disrupting complexes formed between particles of the first and second populations.
Figure 2D:
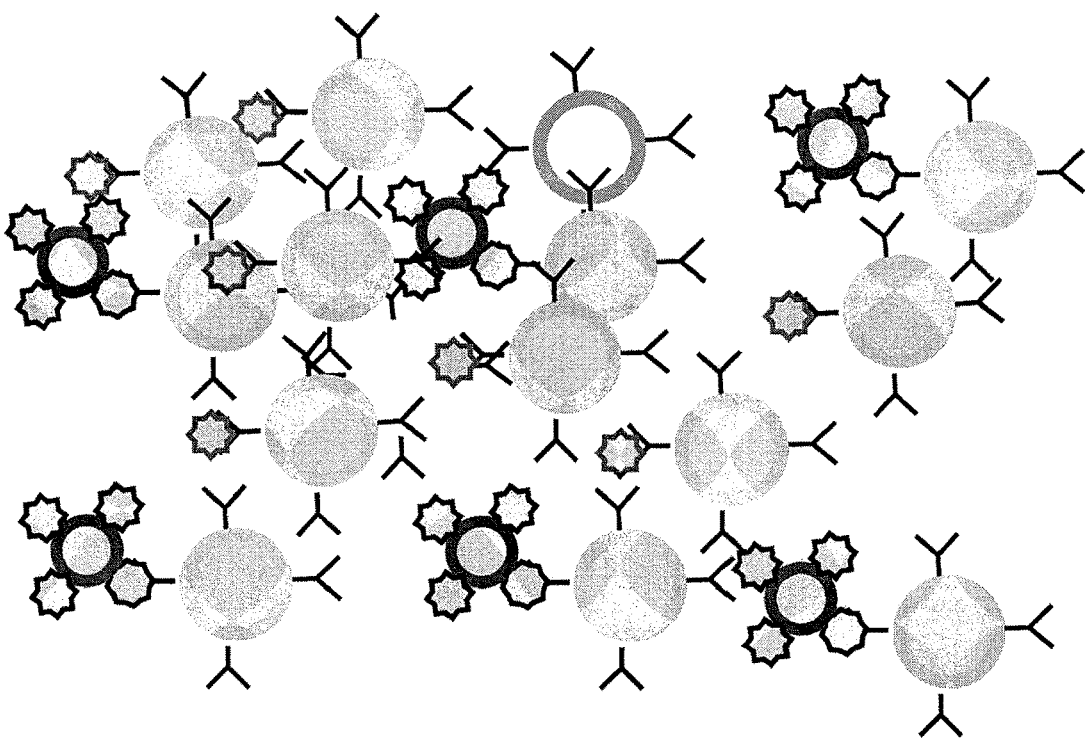
FIG. 2d shows how the application of force, such as gravity or centrifugal force, can lead to separation of first and second particles, with the larger particles leaving solution to form a pellet along with any complexes that include the larger particles.
Figure 2D:
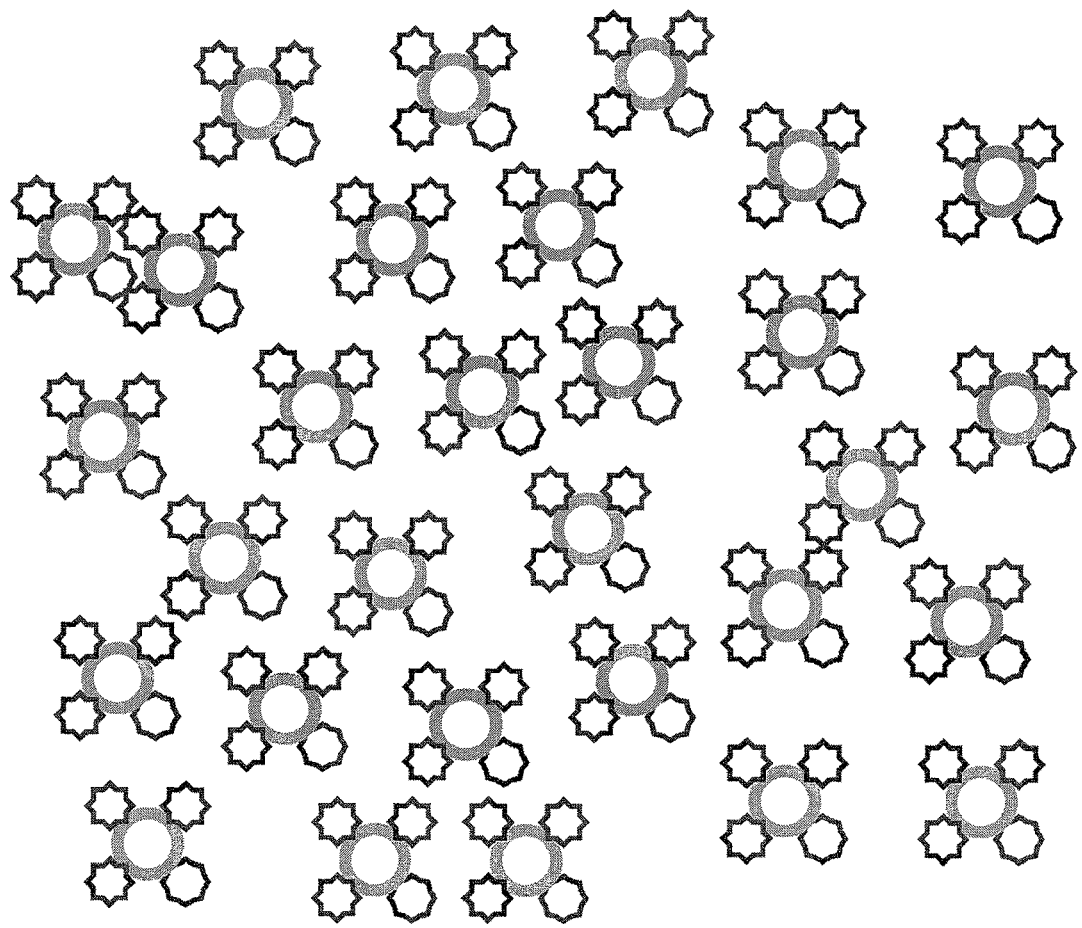
Figure 2E:
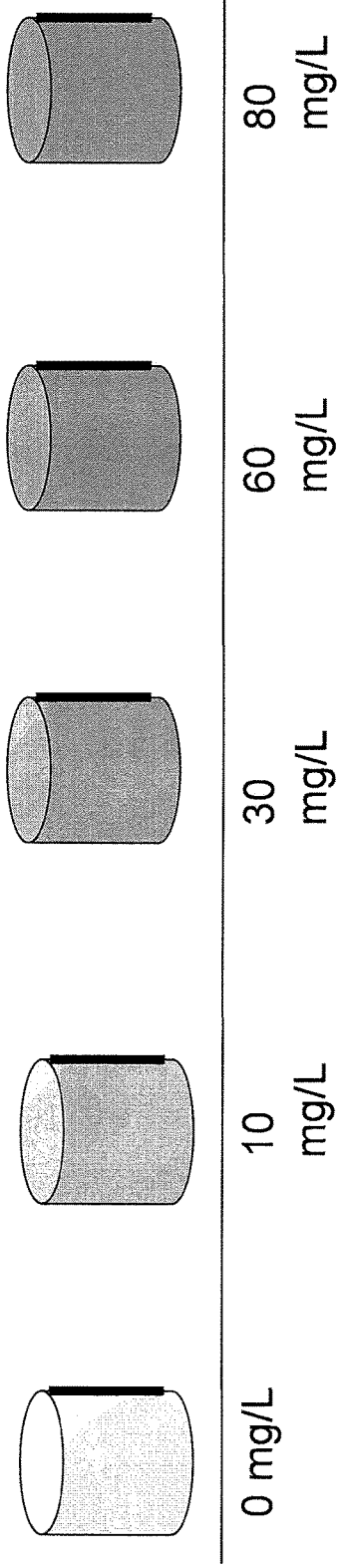
FIG. 2e shows one relationship between (1) the absorbance of the mixture of first and second particles and free analyte, and (2) the concentration of free analyte in the mixture, following the application of an appropriate force. Initially, the absorbance of the mixture goes up as the free analyte concentration goes up, reflecting the fact that increased analyte concentration leads to decreased complex formation, and thus fewer complexes being pelletted upon application of force.
Figure 2E:
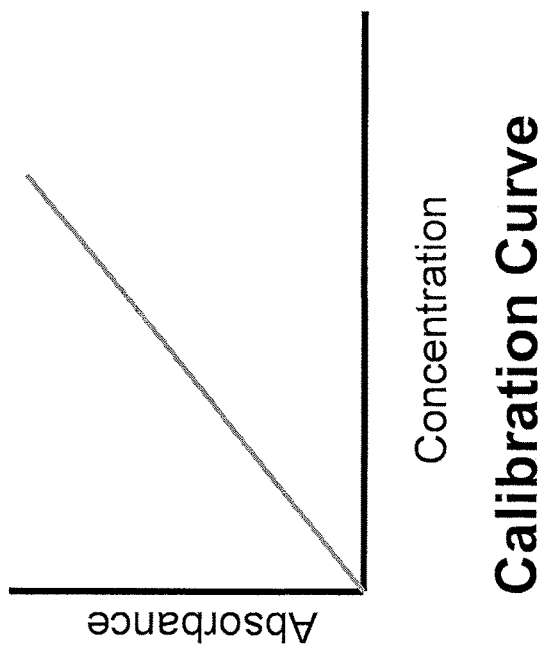

As used herein, the following terms shall have the following meanings.

The term "analyte" refers to a substance potentially present in a sample that can be detected and/or quantified by means of an analytical procedure. Analytes that can be detected using the methods of the invention include, but are not limited to, antigens (e.g., disease-related antigens), antibodies (e.g., disease-related antibodies), macromolecules (e.g., proteins, nucleic acids, carbohydrates, lipids, and combinations thereof), complexes (e.g., multi-protein complexes, nucleoprotein complexes, complexes comprising carbohydrates, lipids, prosthetic groups or other small molecules, etc.), particles (e.g., viral particles or apoptotic bodies), vesicles, cells, and fragments thereof. As used herein, a "complex analyte" is an analyte that consists of a complex (e.g., a multi-protein complex, nucleoprotein complexes, macromolecular complex, etc.).

The term "antibody" refers to a protein comprising an immunoglobulin domain and an antigen binding site. Thus, the term includes, but is not limited to, complete antibodies of any isotype (e.g., IgG, IgM, IgA, IgE, IgD), fragments thereof (e.g., Fab, Fab$^2$, Fc), single-chain antibodies (e.g., Fv), modified antibodies, and fusion proteins comprising an immunoglobulin domain and an antigen binding site.

The term "protein" is used interchangeably with the term "polypeptide" and encompasses full-length proteins, protein domains, protein fragments, mutant proteins, and modified proteins (e.g., proteins comprising chemically modified amino acids or non-naturally occurring amino acids).

The terms "nucleic acid," "oligonucleotide," and "polynucleotide" are used interchangeably and encompass DNA, RNA, and cDNA, whether single-stranded or double-stranded, as well as nucleic acids comprising chemically modified bases or non-naturally occurring bases (e.g., LNA, PNA, etc.).

Additional terms shall be defined, as needed, in the detailed description that follows.

Methods

The present invention is based, in part, on the discovery that particles having different physical or physico-chemical properties, such as buoyancy, size, density, spectral characteristics and/or binding properties, can be used in solution-based sandwich assays for rapid, qualitative and/or quantitative detection of analytes. The present invention is also based, in part, on the discovery that particles having different physical or physico-chemical properties, such as buoyancy, size, density, spectral characteristics and/or binding properties, can be used in solution-based competition assays for rapid, qualitative and/or quantitative detection of analytes.

Accordingly, in one aspect, the present invention provides methods of detecting an analyte in a sample. The methods comprise mixing a sample with a population of first particles and a population of second particles to form a suspension. As used herein, the term "suspension" refers to a liquid mixture in which first and second particles are able to interact with one another and with any analyte that may be present in a sample. As used herein, the term "interact," as it relates to particles and analytes, means to collide and, if appropriate, bind (e.g., form non-covalent or covalent chemical bonds) to one another.

Typically, the first particles and/or the second particles are nanoparticles, nanotubes, hollow nanospheres, or core-shell structure particles. In certain embodiments, the first particles and/or the second particles are colloidal nanoparticles, nanotubes, hollow nanospheres, or core-shell structure particles. As used herein, the terms "colloidal nanoparticles," "colloidal hollow nanospheres," and "colloidal core-shell structure particles" refer to nanoparticles, hollow nanospheres, and core-shell structure particles, respectively, that have a diameter of about 1 nm to about 500 nm and remain in suspension in aqueous media. As used herein, the term "colloidal nanotube" refers to nanotubes that have a diameter of about 1 nm to about 500 nm and a length of about 1 nm to about 500 nm and remain in suspension in aqueous media. In general, colloidal nanoparticles, nanotubes, hollow nanospheres, or core-shell structure particles maintain a homogenous appearance, but do not dissolve, in aqueous media.

In certain embodiments, the first particles comprise gold, silver, platinum, a metal having similar properties, or a composite thereof. In certain embodiments, the first and second particles comprise gold, silver, platinum, a metal having similar properties, or a composite thereof. For example, in certain embodiments, the first and/or second particles are colloidal nanoparticles, nanotubes, hollow nanospheres, or core-shell structure particles that comprise gold, silver, platinum, a metal having similar properties, or a composite thereof. In certain embodiments, the first particles comprise latex, polystyrene, polycarbonate, polyvinylidene fluoride, silica, a polymer having properties similar to any of the foregoing polymers, or a composite thereof. In certain embodiments, the first and second particles comprise latex, polystyrene, polycarbonate, polyvinylidene fluoride, silica, a polymer having properties similar to any of the foregoing polymers, or a composite thereof. In certain related embodiments, the first and/or second particles are colloidal nanoparticles, nanotubes, hollow nanospheres, or core-shell structure particles that comprise latex, polystyrene, polycarbonate, polyvinylidene fluoride, silica, a polymer having properties similar to any of the foregoing polymers, or a composite thereof.

In certain embodiments, the first and second particles have different compositions. For example, in certain embodiments, the first particles comprise gold, silver, platinum, a metal having similar properties, or a composite thereof, and the second particles comprise latex, polystyrene, polycarbonate, polyvinylidene fluoride, silica, a polymer having properties similar to any of the foregoing polymers, or a composite thereof.

In certain embodiments, the first and second particles have different sizes. For example, in certain embodiments, the first particles have an average diameter of about 1 nm to about 200 nm and the second particles have an average diameter of about 200 nm to about 2000 nm. In certain embodiments, the first particles have an average diameter of about 2 nm to about 150 nm, about 3 nm to about 100 nm, about 4 nm to about 70 nm, or about 5 nm to about 40 nm, and the second particles have an average diameter of about 220 nm to about 1800 nm, about 240 nm to about 1600 nm, about 260 nm to about 1400 nm, about 280 nm to about 1200 nm, about 300 nm to about 1000 nm, about 320 nm to about 900 nm, about 340 nm to about 800 nm, about 350 nm to about 700 nm, about 360 nm to about 600 nm, about 370 nm to about 500 nm, about 380 nm to about 450 nm, about 390 nm to about 425 nm, or about 400 nm.

In certain embodiments, the first particles are colloidal nanoparticles, nanotubes, hollow nanospheres, or core-shell structure particles that comprise gold, silver, platinum, a metal having similar properties, or a composite thereof, and have an average diameter of about 1 nm to about 200 nm, about 2 nm to about 150 nm, about 3 nm to about 100 nm, about 4 nm to about 70 nm, or about 5 nm to about 40 nm. In certain embodiments, the second particles comprise latex, polystyrene, polycarbonate, polyvinylidene fluoride, silica, a polymer having properties similar to any of the foregoing polymers, or a composite thereof, and have an average diameter of about 200 nm to about 2000 nm, about 220 nm to about 1800 nm, about 240 nm to about 1600 nm, about 260 nm to about 1400 nm, about 280 nm to about 1200 nm, about 300 nm to about 1000 nm, about 320 nm to about 900 nm, about 340 nm to about 800 nm, about 350 nm to about 700 nm, about 360 nm to about 600 nm, about 370 nm to about 500 nm, about 380 nm to about 450 nm, about 390 nm to about 425 nm, or about 400 nm.

In certain embodiments, the second particles have an average diameter that is about 2 times larger than the average diameter of the first particles. In other embodiments, the second particles have an average diameter that is about 3, 4, 5, 6, 7, 8, 9, 10, 15, 20, 25, 30, 35, 40, 45, 50, 60, 70, 80, 90, 100, or more times larger than the average diameter of the first particles.

In certain embodiments, the first particles are colloidal nanoparticles, nanotubes, hollow nanospheres, or core-shell structure particles that comprise gold, silver, platinum, a metal having similar properties, or a composite thereof, and have an average diameter about 2 to about 100, about 3 to about 80, about 4 to about 65, about 5 to about 50 times smaller than the average diameter of the second particles. In certain embodiments, the second particles comprise latex, polystyrene, polycarbonate, polyvinylidene fluoride, silica, a polymer having properties similar to any of the foregoing polymers, or a composite thereof, and have an average diameter about 2 to about 100, about 3 to about 80, about 4 to about 65, about 5 to about 50 times larger than the average diameter of the first particles.

In certain embodiments, the first and second particles have different densities. For example, in certain embodiments, the first particles have a density about 1.5, 2, 3, 4, 5, 6, 7, 8, 9, 10, or more times greater than the density of the second particles.

In certain embodiments, the first particles are colloidal nanoparticles, nanotubes, hollow nanospheres, or core-shell structure particles that comprise gold, silver, platinum, a metal having similar properties, or a composite thereof, and have a density about 1.5, 2, 3, 4, 5, 6, 7, 8, 9, 10, or more times greater than the density of the second particles. In certain embodiments, the second particles comprise latex, polystyrene, polycarbonate, polyvinylidene fluoride, silica, a polymer having properties similar to any of the foregoing polymers, or a composite thereof, and have a density about 1.5, 2, 3, 4, 5, 6, 7, 8, 9, 10, or more times smaller than the density of the first particles.

In certain embodiments, the first and second particles have different buoyancies in aqueous media. For example, in certain embodiments, the first particles have an average buoyancy about 1.5 to about 250 times greater than the average buoyancy of the second particles. In certain embodiments, the first particles have an average buoyancy about 2 to about 225, about 3 to about 200, about 4 to about 175, about 5 to about 150, about 6 to about 140, about 7 to about 130, about 8 to about 120, about 9 to about 110, about 10 to about 100, about 20 to about 90, about 30 to about 80, about 40 to about 70, about 50 to about 60, or about 55 times greater than the average buoyancy of the second particles.

In certain embodiments, the first particles are colloidal nanoparticles, nanotubes, hollow nanospheres, or core-shell structure particles that comprise gold, silver, platinum, a metal having similar properties, or a composite thereof, and have an average buoyancy about 1.5 to about 250, about 2 to about 225, about 3 to about 200, about 4 to about 175, about 5 to about 150, about 6 to about 140, about 7 to about 130, about 8 to about 120, about 9 to about 110, about 10 to about 100, about 20 to about 90, about 30 to about 80, about 40 to about 70, about 50 to about 60, or about 55 times greater than the average buoyancy of the second particles. In certain embodiments, the second particles comprise latex, polystyrene, polycarbonate, polyvinylidene fluoride, silica, a polymer having properties similar to any of the foregoing polymers, or a composite thereof, and have an average buoyancy about 1.5 to about 250 times, about 2 to about 225, about 3 to about 200, about 4 to about 175, about 5 to about 150, about 6 to about 140, about 7 to about 130, about 8 to about 120, about 9 to about 110, about 10 to about 100, about 20 to about 90, about 30 to about 80, about 40 to about 70, about 50 to about 60, or about 55 times smaller than the average buoyancy of the first particles.

The labels of "first" and "second" particles are used in the foregoing embodiments in a manner that is arbitrary between one embodiment and the next. Thus, although the first particles are described in the various embodiments as having a smaller size, greater density, and greater buoyancy compared to the second particles, these characteristics are not exclusively linked to first particles. For example, first particles can have a smaller size, smaller density, and greater buoyancy compared to second particles. Alternatively, first particles can have a larger size, smaller density, and greater buoyancy compared to second particles. In addition, first particles can have the same size, same density, and/or same buoyancy compared to second particles. Thus, as persons skilled in the art will appreciate, the first and second particles can have any mix of relative physico-chemical properties provided that (1) they have different binding properties and (2) complexes formed between first and second particles have a buoyancy that is sufficiently low as to allow sedimentation of the complexes without concomitant sedimentation of at least the first particles, at least the second particles, or either first or second particles.

In certain embodiments, the first and second particles are capable of forming a multi-particle complex. As used herein, a "multi-particle complex" is any molecular aggregate comprising at least one first particle and at least one second particle, wherein the first and second particles are bound to one another in either a direct or indirect manner. In certain embodiments, the first and second particles are capable of forming a multi-particle complex by means of a direct binding interaction. The term "direct binding," as used in this regard, refers to any binding that does not require an additional molecule separate from the first and second particles to bridge the interaction. Thus, if a first particle has a molecule A covalently bound or otherwise stably linked to its surface and a second particle has a molecule B covalently bound or otherwise stably linked to its surface, the binding of molecule A to molecule B constitutes a direct binding interaction between the first and second particles.

In other embodiments, the first and second particles are capable of forming a complex by means of an indirect binding interaction. The term "indirect binding," as used in this regard, refers to any binding that requires one or more molecules separate from the first and second particles to bridge the interaction. Thus, if a first particle binds to a separate molecule C (e.g., via a molecule A covalently linked to the surface of the particle) and a second particle also binds to a molecule C (e.g., via a molecule B covalently linked to the surface of the particle), the binding of molecule A on a first particle to molecule B on a second particle via intermediate molecule C constitutes an indirect binding interaction between the first and second particles.

In certain embodiments, the first particles, second particles, or both first and second particles comprise an analyte-binding agent, such as an antibody, antigen, polypeptide, polynucleotide, nucleoprotein, aptamer, or ligand (e.g., a carbohydrate, lipid, steroid, vitamin, or other small molecule ligand). Thus, as suitable for solution-based sandwich assays, the first and second particles can comprise different analyte-binding agents. For example, in certain embodiments, the first and second particles comprise analyte-binding agents capable of binding to different parts (e.g., different domains, different epitopes, different subunits or molecules in a complex analyte, etc.) of the same analyte. In certain embodiments, the first and second particles comprise analyte-binding agents capable of simultaneously binding to the same analyte molecule.

Thus, in certain embodiments, the first particles comprise a first antibody capable of recognizing a first epitope on an analyte (e.g., a disease-associated antigen or antibody, a virus or viral antigen, a microorganism or antigen thereof, etc.), the second particles comprise a second antibody capable of recognizing a second epitope on the same analyte, and the first and second epitopes are different (e.g., non-overlapping, or overlapping in a minimal way that does not prevent the analyte from simultaneously binding to a first particle and a second particle). In other embodiments, the first particles comprise a polypeptide capable of binding to a first surface on an analyte (e.g., a disease-associated antigen or antibody, a virus or viral antigen, a microorganism or antigen thereof, etc.), the second particles comprise a polypeptide capable of binding to a second surface on the same analyte, and the first and second surfaces are different (e.g., non-overlapping, or overlapping in a minimal way that does not prevent the analyte from simultaneously binding to a first particle and a second particle). In still other embodiments, the first particles comprise a polynucleotide capable of binding to a first portion of an analyte (e.g., a first portion of a polynucleotide analyte, such as a disease-associated polynucleotide, or a nucleoprotein analyte, such as a viral particle), the second particles comprise a polynucleotide capable of binding to a second portion of the same analyte, and the first and second portions are different (e.g., non-overlapping, or overlapping in a minimal way that does not prevent the analyte from simultaneously binding to a first particle and a second particle).

Persons skilled in the art will recognize that the first and second particles need not comprise the same type of analyte-binding agent, and that many different combinations of first particle analyte-binding agent and second particle analyte-binding agent are possible. Accordingly, the first particle can comprise an antibody while the second particle comprises, for example, an antigen, polypeptide, polynucleotide, nucleoprotein, aptamer, or ligand. Similarly, the first particle can comprise an antigen, while the second particle comprise, for example, an antibody, polypeptide, polynucleotide, nucleoprotein, aptamer, or ligand. Alternatively, the first particle can comprise a polynucleotide while the second particle comprises, for example, an antibody, antigen, polypeptide, nucleoprotein, aptamer, or ligand. And so on.

Alternatively, as suitable for solution-based competition assays, the first particles can comprise an analyte while the second particles comprise a corresponding analyte-binding agent. The analyte can be any type of analyte described herein (e.g., antigens (e.g., disease-related antigens), antibodies (e.g., disease-related antibodies), macromolecules (e.g., proteins, nucleic acids, carbohydrates, lipids, and combinations thereof), complexes (e.g., multi-protein complexes, nucleoprotein complexes, complexes comprising carbohydrates, lipids, prosthetic groups or other small molecules, etc.), particles (e.g., viral particles or apoptotic bodies), vesicles, cells, and fragments thereof). Similarly, the corresponding analyte-binding agent can take many different forms, such as an antibody, polypeptide, polynucleotide, nucleoprotein, aptamer, or ligand (e.g., a carbohydrate, lipid, steroid, vitamin, or other small molecule ligand).

Thus, in certain embodiments, the first particles comprise an antibody (e.g., a disease-related antibody, such as an autoimmune-antibody) while the second particles comprises an antigen recognized by the antibody (e.g., a self antigen). In other embodiments, the first particles comprise a viral antigen or viral particle, while the second particles comprise an antibody, polypeptide, or polynucleotide that specifically binds to the viral antigen and/or viral particle. In still other embodiments, the first particles comprise a disease-related antigen (e.g., an antigen from an infectious microorganism), while the second particles comprise a polypeptide or antibody that binds to the disease-related antigen.

Again, persons skilled in the art will recognize that there are many different combinations of analyte and analyte-binding agents that can be attached to the first and second particles for use in the methods of the invention. Accordingly, the present invention is not limited to the foregoing embodiments, but instead is meant to encompass the many different analyte and analyte-binding agent combinations described or suggested by the present disclosure.

The methods of the invention further comprise removing from the suspension multi-particle complexes formed after mixing the sample with the population of first particles and the population of second particles. In certain embodiments, the multi-particle complexes are removed from the suspension by sedimentation. For example, in certain embodiments, the suspension is allowed to rest for a time sufficient to allow gravity to act upon and thereby sediment (i.e., pellet) the multi-particle complexes. In other embodiments, a force is applied to the suspension to pellet the multi-particle complexes. For example, in certain embodiments, centrifugal force is applied to the suspension, causing any multi-particle complexes present to sediment. In certain embodiments, the suspension is centrifuged (e.g., by spinning the suspension in a rotor) to achieve sedimentation of the multi-particle complexes. In still other embodiments, the multi-particle complexes are removed from the suspension by magnetic force (e.g., when the first or second particles comprise ferromagnetic or paramagnetic materials) or by an electric field (e.g., for charge-based separation of complexes from one or both types of particles).

In certain embodiments, removing multi-particle complexes from the suspension comprises removing from the suspension either first particles (e.g., free first particles and first particles present in a multi-particle complex) or second particles (e.g., free second particles and second particles present in a multi-particle complex). As used herein, a "free first particle" or a "free second particle" is a first particle or a second particle, respectively, that is not part of a multi-particle complex. Since the sedimentation of a particle is directly proportional to the square of the particle diameter (assuming constant particle density), applying a force to the suspension sufficient to sediment first particles or second particles results in sedimentation of larger complexes that comprise one or more of said first or second particles. Thus, the relative buoyancy of first particles and second particles can be selected such that, for a given sedimentation force, either the first particles or the second particles (but not both types of particles) sediment along with any multi-particle complexes comprising one or more of said first particles and one or more of said second particles. Accordingly, in certain embodiments, the methods of the invention comprise removing from the suspension (e.g., by application of an appropriate sedimentation force) either the first particles or the second particles. For example, in certain embodiments, the buoyancy of the first particles is greater than the buoyancy of the second particles and the force applied to the suspension (e.g., centrifugal force) causes sedimentation of second particles (i.e., free second particles and any complexes comprising at least one second particle), but not sedimentation of free first particles.

In other embodiments, removing multi-particle complexes from the suspension does not comprise sedimentation of either first particles (i.e., free first particles) or second particles (i.e., free second particles). For example, in certain embodiments, the force applied to the suspension causes sedimentation of multi-particle complexes but is insufficient to cause sedimentation of either free first particles or free second particles.

In certain embodiments, free first particles remain in suspension at centrifugal forces of about 1400 g or less, about 1500 g or less, about 1600 g or less, about 1700 g or less, about 1800 g or less, about 1900 g or less, about 2000 g or less, about 2100 g or less, about 2200 g or less, about 2300 g or less, about 2400 g or less, or about 2500 g or less.

In certain embodiments, free second particles remain in suspension at centrifugal forces of about 1000 g or less, and sediment out of suspension at centrifugal forces higher than about 1000 g. In certain embodiments, free second particles remain in suspension at centrifugal forces of about 1100 g or less, and sediment out of suspension at centrifugal forces higher than about 1100 g. In certain embodiments, free second particles remain in suspension at centrifugal forces of about 1200 g or less, and sediment out of suspension at centrifugal forces higher than about 1200 g. In certain embodiments, free second particles remain in suspension at centrifugal forces of about 1300 g or less, and sediment out of suspension at centrifugal forces higher than about 1300 g. In certain embodiments, free second particles remain in suspension at centrifugal forces of about 1350 g or less, and sediment out of suspension at centrifugal forces higher than about 1350 g. In certain embodiments, free second particles remain in suspension at centrifugal forces of about 1400 g or less, and sediment out of suspension at centrifugal forces higher than about 1400 g. In certain embodiments, free second particles remain in suspension at centrifugal forces of about 1450 g or less, and sediment out of suspension at centrifugal forces higher than about 1450 g. In certain embodiments, free second particles remain in suspension at centrifugal forces of about 1500 g or less, and sediment out of suspension at centrifugal forces higher than about 1500 g. In certain embodiments, free second particles remain in suspension at centrifugal forces of about 1550 g or less, and sediment out of suspension at centrifugal forces higher than about 1550 g.

In certain embodiments, free first particles remain in suspension at centrifugal forces of about 1000 g or less, while free second particles sediment out of suspension at centrifugal forces of about 500 g to about 1000 g. In certain embodiments, free first particles remain in suspension at centrifugal forces of about 1100 g or less, while free second particles sediment out of suspension at centrifugal forces of about 600 g to about 1100 g. In certain embodiments, free first particles remain in suspension at centrifugal forces of about 1200 g or less, while free second particles sediment out of suspension at centrifugal forces of about 700 g to about 1200 g. In certain embodiments, free first particles remain in suspension at centrifugal forces of about 1300 g or less, while free second particles sediment out of suspension at centrifugal forces of about 800 g to about 1300 g. In certain embodiments, free first particles remain in suspension at centrifugal forces of about 1350 g or less, while free second particles sediment out of suspension at centrifugal forces of about 850 g to about 1350 g. In certain embodiments, free first particles remain in suspension at centrifugal forces of about 1400 g or less, while free second particles sediment out of suspension at centrifugal forces of about 900 g to about 1400 g. In certain embodiments, free first particles remain in suspension at centrifugal forces of about 1450 g or less, while free second particles sediment out of suspension at centrifugal forces of about 950 g to about 1450 g. In certain embodiments, free first particles remain in suspension at centrifugal forces of about 1500 g or less, while free second particles sediment out of suspension at centrifugal forces of about 1000 g to about 1500 g. In certain embodiments, free first particles remain in suspension at centrifugal forces of about 1550 g or less, while free second particles sediment out of suspension at centrifugal forces of about 1050 g to about 1550 g. In certain embodiments, free first particles remain in suspension at centrifugal forces of about 1600 g or less, while free second particles sediment out of suspension at centrifugal forces of about 1100 g to about 1600 g. In certain embodiments, free first particles remain in suspension at centrifugal forces of about 1650 g or less, while free second particles sediment out of suspension at centrifugal forces of about 1150 g to about 1650 g. In certain embodiments, free first particles remain in suspension at centrifugal forces of about 1700 g or less, while free second particles sediment out of suspension at centrifugal forces of about 1200 g to about 1700 g. In certain embodiments, free first particles remain in suspension at centrifugal forces of about 1800 g or less, while free second particles sediment out of suspension at centrifugal forces of about 1300 g to about 1800 g. In certain embodiments, free first particles remain in suspension at centrifugal forces of about 1900 g or less, while free second particles sediment out of suspension at centrifugal forces of about 1400 g to about 1900 g. In certain embodiments, free first particles remain in suspension at centrifugal forces of about 2000 g or less, while free second particles sediment out of suspension at centrifugal forces of about 1500 g to about 2000 g.

In certain embodiments, removing multi-particle complexes from the suspension is achieved by applying a centrifugal force of about 1000 g to about 2500 g to the suspension. In certain embodiments, removing multi-particle complexes from suspension is achieved by applying a centrifugal force of about 1200 g to about 2000 g, about 1350 g to about 2150 g, about 1500 g to about 2300 g, about 1000 g to about 1200 g, about 1100 g to about 1300 g, about 1200 g to about 1400 g, about 1300 g to about 1500 g, about 1400 g to about 1600 g, about 1500 g to about 1700 g, about 1600 g to about 1800 g, about 1700 g to about 1900 g, about 1800 g to about 2000 g, about 1900 g to about 2100 g, about 2000 g to about 2200 g, about 2100 g to about 2300 g, about 2200 g to about 2400 g, or about 2300 g to about 2500 g to the suspension.

In certain embodiments, removing free first particles or free second particles from the suspension is achieved by applying a centrifugal force of about 1000 g to about 2500 g. In certain embodiments, removing first particles or second particles from suspension is achieved by applying a centrifugal force of about 1200 g to about 2000 g, about 1350 g to about 2150 g, about 1500 g to about 2300 g, about 1000 g to about 1200 g, about 1100 g to about 1300 g, about 1200 g to about 1400 g, about 1300 g to about 1500 g, about 1400 g to about 1600 g, about 1500 g to about 1700 g, about 1600 g to about 1800 g, about 1700 g to about 1900 g, about 1800 g to about 2000 g, about 1900 g to about 2100 g, about 2000 g to about 2200 g, about 2100 g to about 2300 g, about 2200 g to about 2400 g, or about 2300 g to about 2500 g to the suspension.

In certain embodiments, applying a centrifugal force of about 1000 g to about 2500 g (e.g., about 1300 g to about 1800 g) to the suspension results in sedimentation of first particles (e.g., free first particles and first particles present in a complex) or second particles (e.g., free second particles and second particles present in a complex), but not both. In certain embodiments, applying a centrifugal force of about 1000 g to about 2500 g (e.g., about 1300 g to about 1800 g) to the suspension does not result in sedimentation of either first particles (i.e., free first particles) or second particles (i.e., free second particles).

The methods of the invention further comprise detecting the presence of first and/or second particles remaining in suspension. For example, in certain embodiments, the first and/or second particles scatter light. In such embodiments, the presence of first and/or second particles in suspension can be detected, e.g., by passing light through the suspension and measuring the amount of light scattering as compared to an equivalent suspension that lacks first and second particles. In other embodiments, the presence of first and/or second particles in suspension can be detected, e.g., by passing light through the suspension and measuring absorbance (e.g., absorbance at a particular wavelength or across a range of wavelengths). In other embodiments, the first and/or second particles comprise a label, such as a fluorescent label. In such embodiments, the presence of first and/or second particles can be detected, e.g., by exciting the fluorescent label and detecting the resulting fluorescence. In related embodiments, the first and second particles can comprise different labels, e.g., fluorescent labels, such as Qdots, having different emission wavelengths, thereby allowing separate detection of the first and second particles. In still other embodiments, the first or second particles comprise a metal (e.g., gold, silver, platinum, a metal having similar properties, or a composite thereof) and are detected using surface-enhanced raman scattering (SERS).

In certain embodiments, detecting the presence of first and/or second particles provides a qualitative assessment. In other embodiments, detecting the presence of first and/or second particles provides a quantitative measurement of the amount of first and/or second particles present. For example, in certain embodiments, measurements of, e.g., light scattering, light absorption, fluorescence/luminescence emission, or SERS, allows for the amount of first and/or second particles remaining in suspension to be determined quantitatively.

In certain embodiments, a decrease in amount of first and/or second particles in suspension is indicative of the presence of the analyte in the sample. For example, in certain embodiments, the assay is a sandwich assay (e.g., a direct or indirect sandwich assay) in which the first and second particles form a complex by binding to the same analyte and a decrease in the amount of first and/or second particles in suspension is indicative of the presence of the analyte in the sample. In other embodiments, an increase in the amount of first and/or second particles in suspension is indicative of the presence of the analyte in the sample. For example, in certain embodiments, the assay is a competition assay in which the first particles comprise an analyte, the second particles comprise a corresponding analyte-binding agent, and an increase in the amount of first and/or second particles in suspension is indicative of the presence of the analyte in the sample. As persons skilled in the art will readily understand, the decrease or increase is relative to an appropriate standard. For example, an appropriate standard will comprise an equivalent amount of first and second particles and an appropriate saline solution or a sample known not to contain the analyte of interest.

In certain embodiments, the analyte is biological analyte. For example, in certain embodiments, the analyte is a pathogenic antigen or an antibody thereto. Suitable pathogenic antigens can originate from viruses (e.g., feline leukemia virus, canine parvovirus, foot and mouth virus, influenza virus, hepatitis a, b, or c virus, HIV virus, human papilloma virus, epstein barr virus, rabies virus, etc.), bacteria (e.g., *Ehrlichia, Borellia, Anthrax, Salmonella, Bacillus*, etc.), fungi, or parasites (e.g., canine heartworm, *Giardia lamblia, Plasmodium falciparum, African trypanosomiasis, Trypanosoma brucei*, etc.). In certain embodiments, the analyte is a disease-related antigen or an antibody thereto. Disease-related antigens include, but are not limited to, cancer-related antigens (e.g., PSA, AFP, CA125, CA15-3, CA19-9, CEA, NY-ESO-1, MUC1, GM3, GD2, ERBB2, etc.), cardiovascular disease-related antigens (e.g., cardiac troponin, C-reactive protein, CK-MB, fatty acid binding protein, etc.), or auto-immune disease-related antigens (e.g., auto-antibodies). In certain embodiments, the analyte is a inflammatory antigen (e.g., C-reactive protein, MRP14, MRP8, 25F9, etc.). In certain embodiments, the analyte is a pregnancy-related antigen (e.g., a fetal antigen).

In other embodiments, the analyte is a non-biological analyte, such as an environmental analyte (e.g., an environmental contaminant).

In certain embodiments, the analyte is present in a biological sample. Biological samples include, but are not limited to, biological fluids (e.g., blood, serum, urine, cerebrospinal fluid, saliva, etc.), tissue homogenates, cell lysates, or extracts thereof. In certain embodiments, the analyte is present in an environmental sample, such as a sample of ground water, river, lake, waste water, etc.

In certain embodiments, the methods of the invention are performed in a container, such as a tube or a cuvette. In certain embodiments, the methods of the invention are performed using a rotor (e.g., a rotor for a centrifuge). In certain embodiments, the container (e.g., tube or cuvette) fits into a rotor. In other embodiments, the container (e.g., tube or cuvette) is built into a rotor. In certain related embodiments, the methods of the invention comprise adding the sample to a rotor that contains the population of first particles and the population of second particles, wherein said mixing occurs in said rotor.

In certain embodiments, the population of first particles is in dry form prior to being mixed with sample. In certain embodiments, the population of second particles is in dry form prior to being mixed with sample. In certain embodiments, both the population of first particles and the population of second particles are in dry form prior to being mixed with sample. The dry form is a lyophilized bead of particles. The size of the bead will depend upon the number and size of the particles in the bead. In certain embodiments, a bead comprises about $10^8$ to about $10^{12}$, about $10^9$ to about $10^{11}$, or about $2 \times 10^9$, about $3 \times 10^9$, about $4 \times 10^9$, about $5 \times 10^9$, about $6 \times 10^9$, about $7 \times 10^9$, about $8 \times 10^9$, about $9 \times 10^9$, about $1 \times 10^{10}$, about $2 \times 10^{10}$, about $3 \times 10^{10}$, about $4 \times 10^{10}$, about $5 \times 10^{10}$, about $6 \times 10^{10}$, about $7 \times 10^{10}$, about $8 \times 10^{10}$, about $9 \times 10^{10}$ particles, wherein the particles have an average diameter of about 10 to about 40 nm. In certain embodiments, a bead comprises about $10^5$ to about $10^9$, about $10^6$ to about $10^8$, or about $2 \times 10^6$, about $3 \times 10^6$, about $4 \times 10^6$, about $5 \times 10^6$, about $6 \times 10^6$, about $7 \times 10^6$, about $8 \times 10^6$, about $9 \times 10^6$, about $1 \times 10^7$, about $2 \times 10^7$, about $3 \times 10^7$, about $4 \times 10^7$, about $5 \times 10^7$, about $6 \times 10^7$, about $7 \times 10^7$, about $8 \times 10^7$, about $9 \times 10^7$ particles, wherein the particles have an average diameter of about 200 to about 500 nm.

In certain embodiments, the population of first particles and the population of second particles are provided in dry form (e.g., as lyophilized beads) in a rotor, wherein the addition of a liquid sample to the rotor results in mixing of the sample with the populations of first and second particles. In certain related embodiments, the population of first particles and the population of second particles are provided separately, e.g., as separate lyophilized beads located within a mixing chamber of a rotor.

Kits

In another aspect, the invention provides kits. In certain embodiments, the kits comprise a population of first particles and a population of second particles, wherein said populations are suitable for use in the methods of the invention. The first and second particles can be any first and second particles described or suggested herein. Accordingly, in certain embodiments, the first and second particles are capable of forming complexes. In certain embodiments, the first and second particles are suitable for use in solution-based competition assays. For example, in certain embodiments, the first and second particles are capable of forming multi-particle complexes wherein free analyte disrupts (e.g., competitively inhibits) formation of said multi-particle complexes. In other embodiments, the first and second particles are suitable for use in solution-based sandwich assays. For example, in certain embodiments, the first and second particles are capable of forming multi-particle complexes comprising a first particle, a second particle, and an analyte. In certain related embodiments, the first and second particles are capable of forming multi-particle complexes, wherein said first particle and said second particle each bind to the same analyte, and wherein said analyte links said first particle to said second particle.

In certain embodiments, the first and/or second particles are detectable in suspension. For example, in certain embodiments, the first and/or second particles scatter light or comprise a detectable color (e.g., visually or spectroscopically detectable color). In certain embodiments, the first and/or second particles comprise a label (e.g., fluorescent label). In certain embodiments, both the first and second particles comprise a label (e.g., different fluorescent labels or different chromophores). In certain embodiments, the first particles comprise a donor chromophore and the second particles comprise an acceptor chromophore, or vice verse, wherein the donor and acceptor chromophores are suitable for detecting interaction between the first and second particles by means of Förster Resonance Energy Transfer (FRET) analysis.

In certain embodiments, the first and/or second particles comprise gold, silver, platinum, a metal having similar properties, or a composite thereof. For example, in certain embodiments, the first and/or second particles are colloidal nanoparticles, nanotubes, hollow nanospheres, or core-shell structure particles that comprise gold, silver, platinum, a metal having similar properties, or a composite thereof. In other embodiments, the first and/or second particles comprise latex, polystyrene, polycarbonate, polyvinylidene fluoride, silica, a polymer having properties similar to any of the foregoing polymers, or a composite thereof. In certain related embodiments, the first and/or second particles are colloidal nanoparticles, nanotubes, hollow nanospheres, or core-shell structure particles that comprise latex, polystyrene, polycarbonate, polyvinylidene fluoride, silica, a polymer having properties similar to any of the foregoing polymers, or a composite thereof.

In certain embodiments, the first particles and the second particles have different physico-chemical properties. For example, in certain embodiments, the first particles have a greater buoyancy than the second particles, or vice versa. In certain embodiments, the first particles are smaller than the second particles, or vice versa. For example, in certain embodiments, the second particles have a diameter about 5 to about 50 times larger than the diameter of the first particles. In other embodiments, the first particles have a diameter about 5 to about 50 times larger than the diameter of the second particles. In certain embodiments, the first particles have a greater density than the second particles, or vice versa. In certain embodiments, the first particles are smaller and more buoyant than the second particles. In certain embodiments, the first particles are smaller, more dense, and more buoyant than the second particles.

In certain embodiments, the first particles comprise an analyte and the second particles comprise a corresponding analyte-binding agent, such as an antibody, antigen, polypeptide, polynucleotide, nucleoprotein, aptamer, or ligand (e.g., a carbohydrate, lipid, steroid, vitamin, or other small molecule ligand). In other embodiments, both the first and second particles comprise an analyte-binding agent, such as an antibody, antigen, polypeptide, polynucleotide, nucleoprotein, aptamer, or ligand (e.g., a carbohydrate, lipid, steroid, vitamin, or other small molecule ligand), wherein the analyte-binding agents bind to the same analyte.

In certain embodiments, the first and second particles comprise different analyte-binding agents. In certain embodiments, the first and second particles comprise analyte-binding agents capable of binding to different parts of the same analyte (e.g., different domains, different epitopes, different subunits or molecules in a complex analyte, etc.). In certain embodiments, the first and second particles comprise analyte-binding agents capable of simultaneously binding to the same analyte. For example, in certain embodiments, the first particles comprise a first antibody capable of recognizing a first epitope on the analyte, the second particles comprise a second antibody capable of recognizing a second epitope on the analyte, and the first and second epitopes are different (e.g., non-overlapping). For example, the first and second epitopes can be on different surfaces of a simple analyte or different subunits or molecules in a complex analyte. In other embodiments, the first particles comprise an antigen capable of being recognized by an analyte (e.g., an antibody analyte, such as a disease-specific antibody or an auto-antibody) and the second particles comprise a protein or antibody capable of recognizing the analyte. For example, the second particle can comprise a protein that is an antibody-binding protein, such as Protein A, Protein G, or Protein L, or an antibody that binds to an antibody constant region (e.g., an anti-IgG or anti-IgM antibody).

In certain embodiments, the population of first particles is in solid (e.g., lyophilized) form. In certain embodiments, the population of second particles is in solid (e.g., lyophilized) form. In certain embodiments, the population of first particles and the population of second particles are in solid (e.g., lyophilized) form.

In certain embodiments, the kit further comprises a container (e.g., a cuvette) that comprises said population of first particles, said population of second particles, or both populations of said first and said second particles. In certain embodiments, the kit further comprises a rotor, wherein said rotor comprises a container (e.g., a cuvette) that comprises said population of first particles, said population of second particles, or both populations of said first and said second particles.

In certain embodiments, the kit further comprises instructions (e.g., instructions for using the contents of the kit to carry out a method of the invention).

Mixtures

In yet another aspect, the invention provides mixtures. In certain embodiments, the mixtures comprise a population of first particles, a population of second particles, and, optionally, an analyte. The first and second particles can be any first and second particles described or suggested herein. Similarly, the analyte can be any analyte described or suggested herein. Accordingly, in certain embodiments, the mixture is part of a solution-based competition assay. For example, in certain embodiments, the first and second particles are capable of forming multi-particle complexes wherein free analyte disrupts (e.g., competitively inhibits) formation of said multi-particle complexes. In other embodiments, mixture is part of a solution-based sandwich assay. For example, in certain embodiments, the first and second particles are capable of forming multi-particle complexes comprising a first particle, a second particle, and an analyte. In certain related embodiments, the first and second particles are capable of forming multi-particle complexes, wherein said first particle and said second particle each bind to the same analyte, and wherein said analyte links said first particle to said second particle.

In certain embodiments, the first and/or second particles are detectable in suspension. For example, in certain embodiments, the first and/or second particles scatter light or comprise a detectable color (e.g., visually or spectroscopically detectable color). In certain embodiments, the first and/or second particles comprise a label (e.g., fluorescent label). In certain embodiments, both the first and second particles comprise a label (e.g., different fluorescent labels or different chromophores). In certain embodiments, the first particles comprise a donor chromophore and the second particles comprise an acceptor chromophore, or vice verse, wherein the donor and acceptor chromophores are suitable for detecting interaction between the first and second particles by means of Förster Resonance Energy Transfer (FRET) analysis.

In certain embodiments, the first and/or second particles comprise gold, silver, platinum, a metal having similar properties, or a composite thereof. For example, in certain embodiments, the first and/or second particles are colloidal nanoparticles, nanotubes, hollow nanospheres, or core-shell structure particles that comprise gold, silver, platinum, a metal having similar properties, or a composite thereof. In other embodiments, the first and/or second particles comprise latex, polystyrene, polycarbonate, polyvinylidene fluoride, silica, a polymer having properties similar to any of the foregoing polymers, or a composite thereof. In certain related embodiments, the first and/or second particles are colloidal nanoparticles, nanotubes, hollow nanospheres, or core-shell structure particles that comprise latex, polystyrene, polycarbonate, polyvinylidene fluoride, silica, a polymer having properties similar to any of the foregoing polymers, or a composite thereof.

In certain embodiments, the first particles and the second particles have different physico-chemical properties. For example, in certain embodiments, the first particles have a greater buoyancy than the second particles, or vice versa. In certain embodiments, the first particles are smaller than the second particles, or vice versa. For example, in certain embodiments, the second particles have a diameter about 5 to about 50 times larger than the diameter of the first particles. In other embodiments, the first particles have a diameter about 5 to about 50 times larger than the diameter of the second particles. In certain embodiments, the first particles have a greater density than the second particles, or vice versa. In certain embodiments, the first particles are smaller and more buoyant than the second particles. In certain embodiments, the first particles are smaller, more dense, and more buoyant than the second particles.

In certain embodiments, the first particles comprise an analyte and the second particles comprise a corresponding analyte-binding agent, such as an antibody, polypeptide, polynucleotide, nucleoprotein, or ligand (e.g., a carbohydrate, lipid, steroid, vitamin, or other small molecule ligand). In other embodiments, both the first and second particles comprise an analyte-binding agent, such as an antibody, polypeptide, polynucleotide, nucleoprotein, or ligand (e.g., a carbohydrate, lipid, steroid, vitamin, or other small molecule ligand), wherein the analyte-binding agents bind to the same analyte.

In certain embodiments, the first and second particles comprise different analyte-binding agents. In certain embodiments, the first and second particles comprise analyte-binding agents capable of binding to different parts of the same analyte (e.g., different domains, different epitopes, etc.). In certain embodiments, the first and second particles comprise analyte-binding agents capable of simultaneously binding to the same analyte. For example, in certain embodiments, the first particles comprise a first antibody capable of recognizing a first epitope on the analyte, the second particles comprise a second antibody capable of recognizing a second epitope on the analyte, and the first and second epitopes are different (e.g., non-overlapping). For example, the first and second epitopes can be on different surfaces of a simple analyte or different subunits or molecules in a complex analyte. In other embodiments, the first particles comprise an antigen capable of being recognized by an analyte (e.g., an antibody analyte, such as a disease-specific antibody or an auto-antibody) and the second particles comprise a protein or antibody capable of recognizing the analyte. For example, the second particle can comprise a protein that is an antibody-binding protein, such as Protein A, Protein G, or Protein L, or an antibody that binds to an antibody constant region (e.g., an anti-IgG or anti-IgM antibody).

The present invention has been illustrated and described in detail with reference to particular embodiments by way of example only, and not by way of limitation. Those of skill in the art will appreciate that various modifications to the disclosed embodiments are within the scope and contemplation of the invention of the present disclosure. Therefore, it is intended that the invention be considered as limited only by the scope of the appended claims.

What is claimed:

1. A method of detecting an analyte in a sample comprising
   mixing a sample with a population of first particles and a population of second particles to form a suspension, wherein the first and second particles are different and capable of forming a multi-particle complex comprising the first particle, second particle, and the analyte,
   removing the multi-particle complexes from the suspension, and
   detecting the presence of free first particles in the suspension after removal of the multi-particle complexes, wherein a decrease of the free first particles in the suspension is indicative of the presence of the analyte in the sample.

2. The method of claim 1, wherein the first particles or second particles comprise an antibody, antigen, polypeptide, polynucleotide, nucleoprotein, or aptamer.

3. The method of claim 1, wherein the first particles comprise a first monoclonal antibody or a first polyclonal antibody recognizing a first epitope on the analyte, wherein the second particles comprise a second monoclonal antibody or a second polyclonal antibody recognizing a second epitope on the analyte, and wherein the first epitope does not overlap with the second epitope.

4. The method of claim 1, wherein the first particles are colloidal nanoparticles, nanotubes, hollow nanospheres, or core-shell structures that comprise gold, silver, platinum, copper, or a composite of any of the foregoing metals.

5. The method of claim 1, wherein the free first particles remain in suspension at centrifugal forces of about 1600 g or less.

6. The method of claim 1, wherein the first particles are smaller than the second particles.

7. The method of claim 1, wherein the first particles are colloidal nanoparticles, nanotubes, hollow nanospheres, or core-shell structures that comprise gold, silver, platinum, copper, or a composite of any of the foregoing metals, and wherein the second particles comprise latex, polystyrene, polycarbonate, polyvinylidene fluoride (PVDF), or silica.

8. The method of claim 1, wherein the free first particles remain in suspension at centrifugal forces of about 1600 g or less, and wherein free second particles sediment out of the suspension at centrifugal forces of about 1000 g to about 1600 g.

9. The method of claim 1, wherein the first particles have an average diameter of about 5 nm to about 40 nm, and wherein the second particles have an average diameter of about 400 nm to about 2000 nm.

10. The method of claim 1, wherein the sample is in a liquid form and wherein the population of first particles and the population of second particles are in solid form prior to the mixing.

11. The method of claim 1, wherein the analyte is canine heartworm, feline leukemia virus, canine parvovirus, C-reactive protein, *Giardia lamblia*, *Ehrlichia* antigen or antibody, *Borrelia* antigen or antibody, and cardiac marker antigens.

12. The method of claim 1, wherein removing the multi-particle complexes comprises using centrifugal force.

13. The method of claim 1, wherein the population of first particles and the population of second particles are separate prior to mixing with the sample.

14. The method of claim 1, wherein the ratio of the average diameter of second particles to the average diameter of first particles is about 5:1 to about 50:1.

* * * * *